Figure 2A:
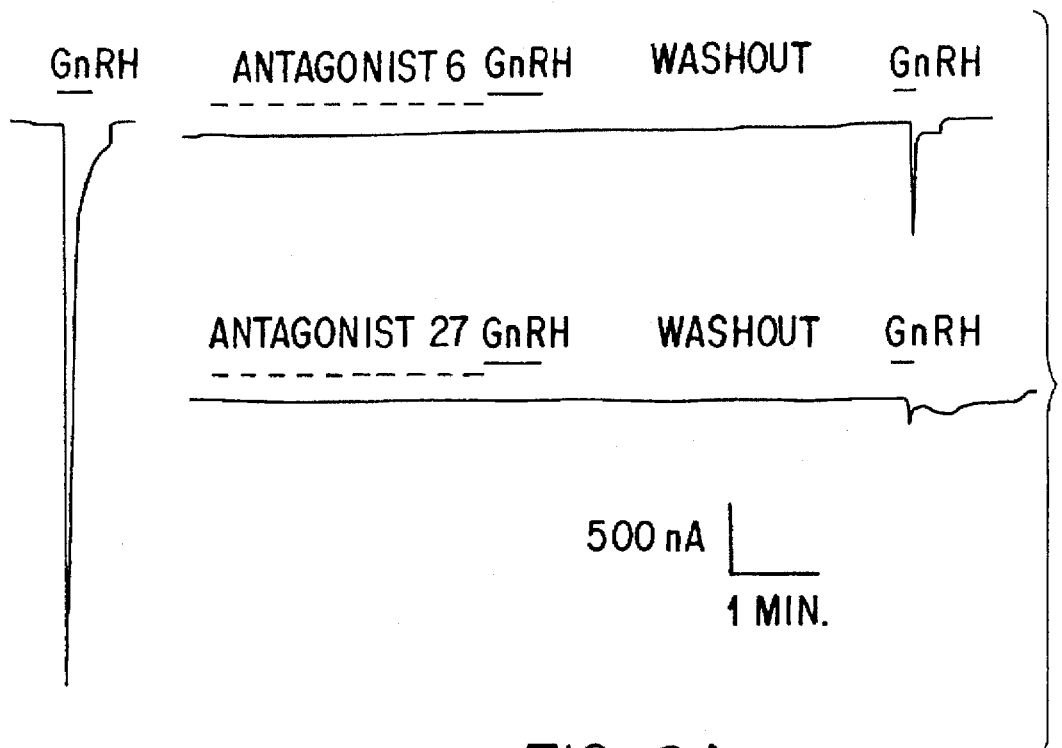

United States Patent [19]

Sealfon

[11] Patent Number: 5,750,366
[45] Date of Patent: May 12, 1998

[54] CLONING AND EXPRESSION OF GONADOTROPIN-RELEASING HORMONE RECEPTOR

[75] Inventor: Stuart C. Sealfon, Brooklyn Heights, N.Y.

[73] Assignee: Mount Sinai School Of Medicine Of The City University Of New York, New York, N.Y.

[21] Appl. No.: 80,386

[22] Filed: Jun. 21, 1993

Related U.S. Application Data

[63] Continuation-in-part of Ser. No. 904,072, Jun. 23, 1992, abandoned.

[51] Int. Cl.$^6$ .................... C07K 14/72; C12N 15/12; C12N 15/63; C07H 21/04
[52] U.S. Cl. .................. 435/69.1; 435/320.1; 435/252.3; 435/325; 536/23.5; 530/350; 935/9
[58] Field of Search ........................... 435/91, 69.1, 69.4, 435/172.1, 320.1, 252.3, 325; 530/387.9, 350, 399; 536/23.5, 23.51; 935/9

[56] References Cited

PUBLICATIONS

Clayton, 1987, "Gonadotrophin Releasing Hormone: from Physiology to Pharmacology," Clinical Endocrinology 26:361–384.

Clayton, 1989, "Gonadotrophin–Releasing Hormone: its Actions and Receptors," Journal of Endocrinology 120:11–19.

Sealfon et al., 1990, "Gonadotropin–Releasing Hormone Receptor Expression in *Xenopus Oocytes*," Molecular Endocrinology 4:119–124.

Probst et al., 1992, "Sequence Alignment of the G–Protein Coupled Receptor Superfamily," DNA and Cell Biology 11:1–20.

Tsutsumi et al., 1992, "Cloning and Functional Expression of a Mouse Gonadotropin–Releasing Hormone Receptor," Molecular Endocrinology 6(7):1163–1169.

Eidne et al., 1992, "Molecular Cloning and Characterization of the Rat Pituitary Gonadotropin–Releasing Hormone (GnRH) Receptor," Molecular and Cellular Endocrinology 90:R5–R9, Oct.

Kakar et al., 1992, "Cloning, Sequencing and Expression of Human Gonadotropin Releasing Hormone (GnRH) Receptor," Biochemical and Biophysical Research Communications 189(1):289–295, Nov.

Chi et al., 1993, "Cloning and Characterization of the Human GnRH Receptor," Molecular and Cellular Endocrinology 91:R1–R6.

*Primary Examiner*—Stephen Walsh
*Assistant Examiner*—Lorraine M. Spector
*Attorney, Agent, or Firm*—Pennie & Edmonds LLP

[57] ABSTRACT

The present invention relates to the GnRH-R genes and proteins. The DNA sequences disclosed herein may be engineered into expression systems designed for the production of GnRH-R and/or cell lines which express the GnRH-R and preferably respond to GnRH induced signal transduction. Such cell lines may advantageously be used for screening and identifying GnRH agonists and antagonists. In accordance with another aspect of the invention, the GnRH DNA, antisense oligonucleotide sequences, the GnRH expression products, and antibodies to such products may be used in the diagnosis and therapy of reproductive disorders associated with abnormal expression of the GnRH-R; e.g., overexpression, underexpression or expression of a dysfunctional mutant receptor. Transgenic animals containing the GnRHR transgene may be used as animal models for the evaluation of GnRH analogs in vivo.

14 Claims, 16 Drawing Sheets

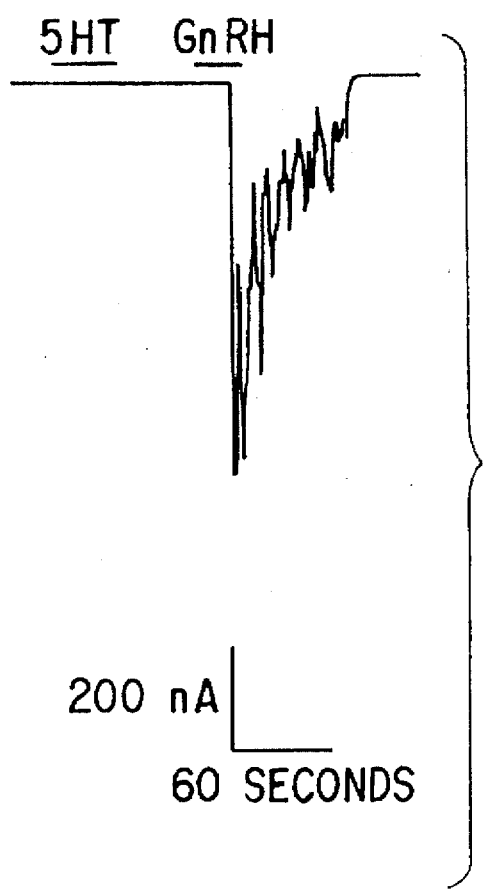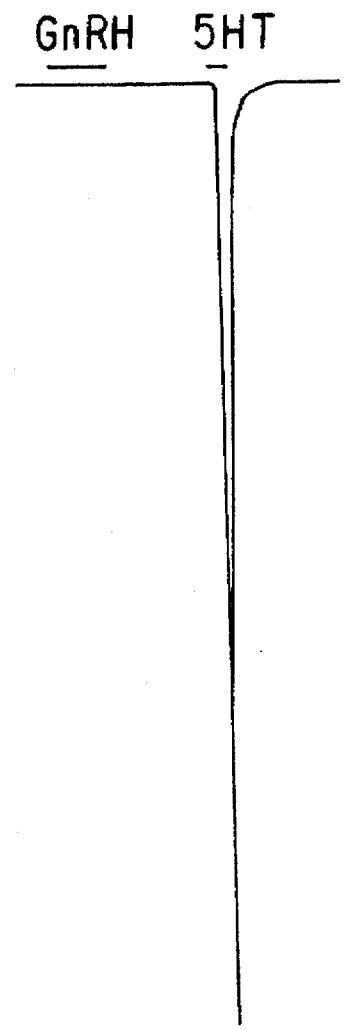
FIG. 1A
FIG. 1B

```
                CACGAGAGGGACTCCACTCTTGAAGCCTGTCCTTGGAGAAAT    -1

ATGGCTAACAATGCATCTCTTGAGCAGGACCCAAATCACTGCTCGGCCATCAACAACAGC    60
 M  A  N  N  A  S  L  E  Q  D  P  N  H  C  S  A  I  N  N  S    20
       ▲                                           ▲
ATCCCCTTGATACAGGGCAAGCTCCCGACTCTAACCGTATCTGGAAAGATCCGAGTGACC    120
 I  P  L  I  Q  G  K  L  P  T  L  T  V  S  G  K  I  R  V  T    40
                                             _____
GTGACTTTCTTCCTTTTCCTACTCTCTACTGCCTTCAATGCTTCCTTCTTGTTGAAGCTG    180
 V  T  F  F  L  F  L  L  S  T  A  F  N  A  S  F  L  L  K  L    60
_____  I

CAGAAGTGGACTCAGAAGAGGAAGAAAGGAAAAAAGCTCTCAAGGATGAAGGTGCTTTTA    240
 Q  K  W  T  Q  K  R  K  K  G  K  K  L  S  R  M  K  V  L  L    80
 _  _  _         *                       ◆ *          _____
AAGCATTTGACCTTAGCCAACCTGCTGGAGACTCTGATCGTCATGCCACTGGATGGATG    300
 K  H  L  T  L  A  N  L  L  E  T  L  I  V  M  P  L  D  G  M    100
 _____  II
TGGAATATTACTGTTCAGTGGTATGCTGGGGAGTTCCTCTGCAAAGTTCTCAGCTATCTG    360
 W  N  I  T  V  Q  W  Y  A  G  E  F  L  C  K  V  L  S  Y  L    120
    ▲                                        _____
AAGCTCTTCTCTATGTATGCCCCAGCTTTCATGATGGTGGTGATTAGCCTGGACCGCTCC    420
 K  L  F  S  M  Y  A  P  A  F  M  M  V  V  I  S  L  D  R  S    140
 _____  _____         *
         III
CTGGCCATCACTCAGCCCCTTGCTGTACAAAGCAACAGCAAGCTTGAACAGTCTATGATC    480
 L  A  I  T  Q  P  L  A  V  Q  S  N  S  K  L  E  Q  S  M  I    160
                             •                    _____
AGCCTGGCCTGGATTCTCAGCATTGTCTTTGCAGGACCACAGTTATATATCTTCAGGATG    540
 S  L  A  W  I  L  S  I  V  F  A  G  P  Q  L  Y  I  F  R  M    180
 _____ IV _____
ATCTACCTAGCAGACGGCTCTGGGCCCACAGTCTTCTCGCAATGTGTGACCCACTGCAGC    600
 I  Y  L  A  D  G  S  G  P  T  V  F  S  Q  C  V  T  H  C  S    200

TTTCCACAGTGGTGGCATCAGGCCTTCTACAACTTTTTCACCTTCGGCTGCCTCTTCATC    660
 F  P  Q  W  W  H  Q  A  F  Y  N  F  F  T  F  G  C  L  F  I    220
                          _____  ____
                                                    V
ATCCCCCTCCTCATCATGCTAATCTGCAATGCCAAAATCATCTTTGCTCTCACGCCAGTC    720
 I  P  L  L  I  M  L  I  C  N  A  K  I  I  F  A  L  T  R  V    240
 _____        *
CTTCATCAAGACCCACGCAAACTACAGATGAATCAGTCCAAGAATAATATCCCAAGAGCT    780
 L  H  Q  D  P  R  K  L  Q  M  N  Q  S  K  N  N  I  P  R  A    260
```

FIG.3A

```
CGGCTGAGAACGCTAAAGATGACAGTCGCATTCGCTACCTCCTTTGTCGTCTGCTGGACT  840
 R  L  R  T  L  K  M  T  V  A  F  A  T  S  F  V  V  C  W  T   280
       *              ─────────────────────────────────────
                                                        VI ──
CCCTACTATGTCCTAGGCATTTGGTACTGGTTTGATCCAGAAATGTTGAACAGGGTGTCA  900
 P  Y  Y  V  L  G  I  W  Y  W  F  D  P  E  M  L  N  R  V  S   300
─────────────────────────────

GAGCCAGTGAATCACTTTTTCTTTCTCTTTGCTTTCCTAAACCCGTGCTTCGACCCACTC  960
 E  P  V  N  H  F  F  F  L  F  A  F  L  N  P  C  F  D  P  L   320
          ───────────────── ─────────────────────────────
                        VII

ATATATGGGTATTTCTCTTTGTAGTTGGGAGACTACACAAGAACTCAGATAGAAATAAGG 1020
 I  Y  G  Y  F  S  L                                           327
 ─────────────────

TAACTAATTGCACCAATTGAGAATAAACTCAAAGCTTTTGACACACTTATATACAAGGCA 1080
GGGTTTAAGGTTAGATTATCAACCTTGTTTTTGTACAGAGTTTGTTGTTAGAGCTTCAGA 1140
AGACCTTCAAAAACAAAAAAAAAAAAAAAAAAAAAAAAAAAAAAA                1185
```

FIG. 3B

```
     I
GnR          MANNASLEQDPNHCSAINNSIPLIQKLPTLTVSGKIRVTVTEFLFLLSTAFNASFLLKLQKWTQKR
ILR   MESDSFEDFWKGEDLSNYSYSSTLPPFLLDAAPCEPESLEINKYFVVIYALVFLLSLLGNSLVMLVILYSRVGR
SPR                MDNVLPMDSDLFPNISTNTSESNQFVQPTWQIVLWAAAYTVIVTSVVGNVVVIWIILAHKRMR
β1R  (9)ASEPGNLSSAAPLPDGAATAARLLVPASPPASLLPPASESPPELSQQWTAGMGLLMALIVLLIVAGNVLVIVAIAKTPRLQ
RHD                     MNGTEGPNFYVPFSNATGVVRSPFEYPQYYLAEPWQFSMLAAYM-FLQIVLGFPINFLTLYVTVQHKKLR

III
GnR  KKGKKLSRMKVLLKHLTLANLLETLIVMPLDGMWNITVQWYAGEFLCKVLSYLKLFSMYAPAFMMVISLDRSLAITQPLAVQSN
ILR  SVTD------VYLLNLALADLLFALILTLPIWAASKVNGWIF--GTFLCKVWSLLKEVNFLYSGILLLACISVDRYLAIVHATRLTLTQ
SPR  TVTN------YFLVNLAFAEACMAAFNTVVNFTYAVHNVWYYQLFYCKFHNFFPIAALFASIYSMTAVAFDRYMAILHPLQPRLS
β1R  TLTN------LFIMSLASADLVMGLLVVPFGATIVVWGRWEYGSFFCELWTSVDVLCVTASIETLCVIALDRYLAITSPFRYQSL
RHD  TPLN------YILLNLAVADLFMVLGGFTSTLYTSLHGYFVFGPTGCNLEGFFATLGGEIALWSLVVLAIERYVVCKPMSNFRF

V
GnR  --SKLEQSMISLAWILSIVFAGPQLYIFRMIYLADGSGPTVFSQCVTH-CSFPQWWHQAFYNFFTFEGCLFIPLLIMLICNAKIIFALTR
ILR  -KRYLVKFICLSIWGLSLLIALPVLFRRITVYSSN----VSPACYED-MGNNTANWRMLLRILPQSFGFJVPLLIMLFCYGFTLRTLFK
SPR  --ATATKVVIFVIWVLALLLAFPQGYYSTTETMPS----RVVCMIEWPEHQNRTYEKAYHICVTVLIYFLPLLVIAYAYTVVGITLWA
β1R  LTRARARGLVCTVWAISALVSFLPILMHWRAESD-----EARRCYNDPKCCD-FVTNRAYAIASSVVSFYVPLCIMAFVYLRVFREAQK
RHD  -GENHAIMGVAFTWVMALACAAPPLAGWSRYIPEG----LQCSCGIDYTLKPEVNNESFVIYMFVVHFIIPMIIIFFCYGQLVFTVKE
```

FIG. 4B

```
                                                              VI
GnR   VLHQD-------------------PRKLQMNQSKNNIPRARLRTLKMTVAFATSFVVCWTPYYVLGIWYWFDPEMLNRV
ILR   AHMGQ----------------------KHRAMRVIFAVVLIFLLCWLPYNLVLLADTLMRTQVIQE
SPR   SEIPG------------------------DSSDRYHEQVSAKRKVVKMIVVVCTFAICWLPFHVFLLPYINEDLYLKK
β1R   QVKKIDSCERRFLGGPARPPSPSP.(20).TAPLANGRAGKRRPSRLVALREQKALKTLGIMGVFTLCWLPFFLANVVKAEH
RHD   -------------------------------AAAQQQESATTQKAEKEVTRMVIIMVIAFLICWVPYASVAFYIFTHQGSNFGPI

VII
GnR   --------SEPVNHFFFLFAFLNPCFDPLIYGYFSL
ILR   TCERRNHIDRALDATEILGILHSCLNPLIYAFIGQKFRHGLLKILAIHGLISKDSLPKDSRPSFVGSSSGHTSTTL
SPR   ----FIQQVYLASMWLAMSSTMYNPIIYCCLNDRFRLGFKHAFRCCPFISAGDYEGLEMKSTRYLQTQSSVYKVSRLETTISTVVG(43)
β1R   ---RELVPDRLFVFFNWLGYANSAFNPIIYCRSPDFRKAFQGLLCCARRAARRHATHGDRPRASGCLARPPPSPGAASDDDDDDV(43)
RHD   ------FMTIPAFFAKSAAIYNPVIYIMMNKQFRNCMLTTICCGKNPLGDDEASATVSKTETSQVAPA
```

FIG. 4C

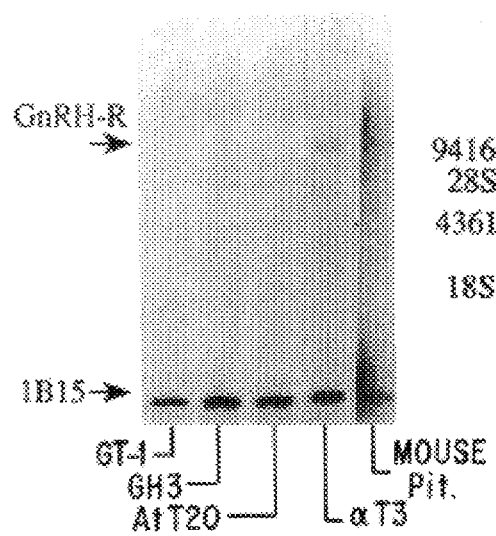
FIG. 5A
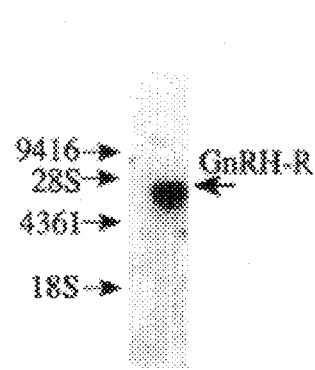
FIG. 5B
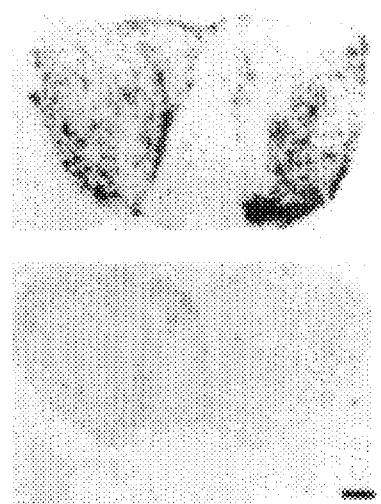
FIG. 5C
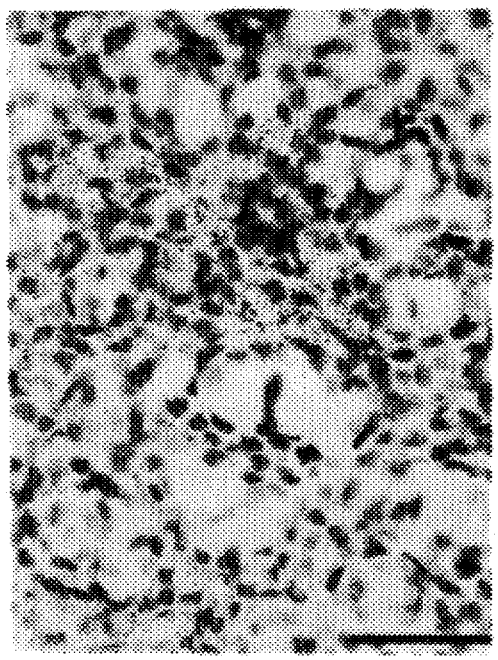
FIG. 5E
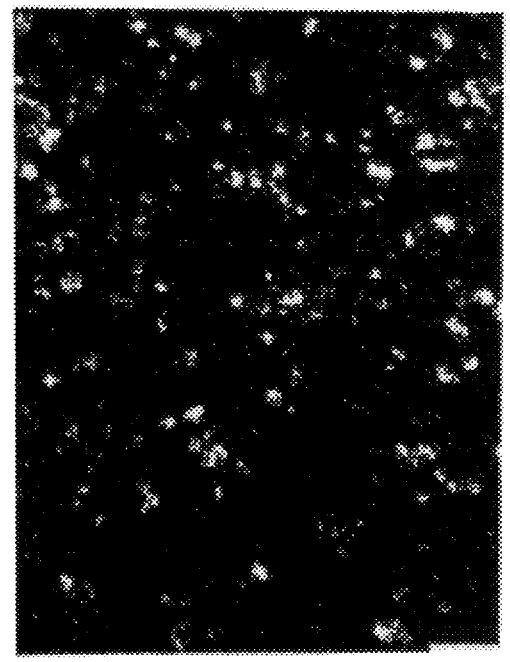
FIG. 5F
FIG. 5D

```
                                              CGGAGCCTTGTGTCCTGGGAAAAT    -1
ATGGCAAACAGTGCCTCTCCTGAACAGAATCAAAATCACTGTTCAGCCATCAACAACAGC             60
 M   A   N   S   A   S   P   E   Q   N   Q   N   H   C   S   A   I   N   N   S      20
ATCCCACTGATGCAGGGCAACCTCCCCACTCTGACCTTGTCTGGAAAGATCCGAGTGACG            120
 I   P   L   M   Q   G   N   L   P   T   L   T   L   S   G   K   I   R   V   T      40
GTTACTTTCTTCCTTTTTCTGCTCTCTGCGACCTTTAATGCTTCTTTCTTGTTGAAACTT            180
 V   T   F   F   L   F   L   L   S   A   T   F   N   A   S   F   L   L   K   L      60
CAGAAGTGGACACAGAAGAAAGAGAAAGGGAAAAAGCTCTCAAGAATGAAGCTGCTCTTA            240
 Q   K   W   T   Q   K   K   E   K   G   K   K   L   S   R   M   K   L   L   L      80
AAACATCTGACCTTAGCCAACCTGTTGGAGACTCTGATTGTCATGCCACTGGATGGGATG            300
 K   H   L   T   L   A   N   L   L   E   T   L   I   V   M   P   L   D   G   M     100
TGGAACATTACAGTCCAATGGTATGCTGGAGAGTTACTCTGCAAAGTTCTCAGTTATCTA            360
 W   N   I   T   V   Q   W   Y   A   G   E   L   L   C   K   V   L   S   Y   L     120
AAGCTTTTCTCCATGTATGCCCCAGCCTTCATGATGGTGGTGATCAGCCTGGACCGCTCC            420
 K   L   F   S   M   Y   A   P   A   F   M   M   V   V   I   S   L   D   R   S     140
CTGGCTATCACGAGGCCCCTAGCTTTGAAAAGCAACAGCAAAGTCGGACAGTCCATGGTT            480
 L   A   I   T   R   P   L   A   L   K   S   N   S   K   V   G   Q   S   M   V     160
GGCCTGGCCTGGATCCTCAGTAGTGTCTTTGCAGGACCACAGTTATACATCTTCAGGATG            540
 G   L   A   W   I   L   S   S   V   F   A   G   P   Q   L   Y   I   F   R   M     180
ATTCATCTAGCAGACAGCTCTGGACAGACAAAAGTTTTCTCTCAATGTGTAACACACTGC            600
 I   H   L   A   D   S   S   G   Q   T   K   V   F   S   Q   C   V   T   H   C     200
AGTTTTTCACAATGGTGGCATCAAGCATTTATAACTTTTTCACCTTCAGCTGCCTCTTC             660
 S   F   S   Q   W   W   H   Q   A   F   Y   N   F   F   T   F   S   C   L   F     220
ATCATCCCTCTTTTCATCATGCTGATCTGCAATGCAAAAATCATCTTCACCCTGACACGG            720
 I   I   P   L   F   I   M   L   I   C   N   A   K   I   I   F   T   L   T   R     240
GTCCTTCATCAGGACCCCCACGAACTACAACTGAATCAGTCCAAGAACAATATACCAAGA            780
 V   L   H   Q   D   P   H   E   L   Q   L   N   Q   S   K   N   N   I   P   R     260
GCACGGCTGAAGACTCTAAAAATGACGGTTGCATTTGCCACTTCATTTACTGTCTGCTGG            840
 A   R   L   K   T   L   K   M   T   V   A   F   A   T   S   F   T   V   C   W     280
ACTCCCTACTATGTCCTAGGAATTTGGTATTGGTTTGATCCTGAAATGTTAAACAGGTTG            900
 T   P   Y   Y   V   L   G   I   W   Y   W   F   D   P   E   M   L   N   R   L     300
TCAGACCCAGTAAATCACTTCTTCTTTCTCTTTGCCTTTTTAAACCCATGCTTTGATCCA            960
 S   D   P   V   N   H   F   F   F   L   F   A   F   L   N   P   C   F   D   P     320
CTTATCTATGGATATTTTTCTCTGTGATTGATAGACTACACAAGAAGTCATATGAAGAAG           1020
 L   I   Y   G   Y   F   S   L   *                                                 328
GGTAAGGTAATGAATCTCTCCATCTGGGAATGATTAACACAAATGTTGGAGCATGTTTAC           1080
ATACAAACAAAGTAGGATTTACACTTAAGTTATCATTCTTTTAGAAACTCAGTCTTCAGA           1140
GCCTCAATTATTAAGGAAAAGTCTTCAGGAAAAATACTAAAATATTTTCTCTTCCTCATA           1200
AGCTTCTAAATTAATCTCTGCCTTTTCTGACCTCATATAACACATTATGTAGGTTTCTTA           1260
```

FIG.9A

```
TCACTTTCTCTTTGCATAATAATGTACTAATATTTAAAATACCTTCAGCCTAAGGCACAA    1320
GGATGCCAAAAAAACAAAGGTGAGAACCCACAACACAGGTCTAAACTCAGCATGCTTGGT    1380
GAGTTTTCTCCAAAGGGGCATATTAGCAATTAGAGTTGTATGCTATATAATACATAGAG    1440
CACAGAGCCCTTTGCCCATAATATCAACTTTCCCTCCTATAGTTAAAAAGAAAAAAAAAT    1500
GAATCTATTTTTCTCTTTGGCTTCAAAAGCATTCTGACATTTGGAGGAGTCAGTAACCAA    1560
TCCCACCAACCACTCCAGCAACCTGACAAGACTATGAGTAGTTCTCCTTCATCCTATTTA    1620
TGTGGTACAGGTTGTGAAGTATCTCTATATAAAGGGAAATTTTAGAGGGGTTAGGATTTG    1680
GACAGGGGTTTAGAACATTCCTCTAAGCTATCTAGTCTGTGGAGTTTGTGGCAATTAATT    1740
GCCATAAAATAACATGTTTCCAAATGCAACTAAGAAAATACTCATAGTGAGTACGCTCTA    1800
TGCATAGTATGACTTCTATTTAATGTGAAGAATTTTTTGTCTCTCTCCTGATCTTACTAA    1860
ATCCATATTTCATAAATGAACTGAGAATAATTAACAAAATTAAGCAAATGCACAAGCAAA    1920
AGATGCTTGATACACAAAAGGAACTCTGGAGAGAAAACTACAGCTTCAGTCTGTACAGAT    1980
CAAAGAAGACAGAACATGTCAGGGGAAGGAGGAAAGATCTTGATGCAGGGTTTCTTAACC    2040
TGCAGTCTATGCACAACACTATATTTCCATGTAATGTTTTTATTTCAGCCCTATTTGTAT    2100
TATTTTGTGCATTTAAAAAACACAATCTTAAGGCCG    2136
```

FIG.9B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1227 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 43..1023

( x i ) SEQUENCE DESCRIPTION: SEQ ID NO:1:

```
CACGAGAGGG  ACTCCACTCT  TGAAGCCTGT  CCTTGGAGAA  AT  ATG  GCT  AAC  AAT            54
                                                   Met Ala  Asn  Asn
                                                    1

GCA  TCT  CTT  GAG  CAG  GAC  CCA  AAT  CAC  TGC  TCG  GCC  ATC  AAC  AAC  AGC  102
Ala  Ser  Leu  Glu  Gln  Asp  Pro  Asn  His  Cys  Ser  Ala  Ile  Asn  Asn  Ser
 5                   10                  15                          20

ATC  CCC  TTG  ATA  CAG  GGC  AAG  CTC  CCG  ACT  CTA  ACC  GTA  TCT  GGA  AAG  150
Ile  Pro  Leu  Ile  Gln  Gly  Lys  Leu  Pro  Thr  Leu  Thr  Val  Ser  Gly  Lys
                     25                  30                          35

ATC  CGA  GTG  ACC  GTG  ACT  TTC  TTC  CTT  TTC  CTA  CTC  TCT  ACT  GCC  TTC  198
Ile  Arg  Val  Thr  Val  Thr  Phe  Phe  Leu  Phe  Leu  Leu  Ser  Thr  Ala  Phe
              40                          45                  50

AAT  GCT  TCC  TTC  TTG  TTG  AAG  CTG  CAG  AAG  TGG  ACT  CAG  AAG  AGG  AAG  246
Asn  Ala  Ser  Phe  Leu  Leu  Lys  Leu  Gln  Lys  Trp  Thr  Gln  Lys  Arg  Lys
```

```
                    55                          60                              65
AAA  GGA  AAA  AAG  CTC  TCA  AGG  ATG  AAG  GTG  CTT  TTA  AAG  CAT  TTG  ACC       294
Lys  Gly  Lys  Lys  Leu  Ser  Arg  Met  Lys  Val  Leu  Leu  Lys  His  Leu  Thr
          70                        75                        80

TTA  GCC  AAC  CTG  CTG  GAG  ACT  CTG  ATC  GTC  ATG  CCA  CTG  GAT  GGG  ATG       342
Leu  Ala  Asn  Leu  Leu  Glu  Thr  Leu  Ile  Val  Met  Pro  Leu  Asp  Gly  Met
85                        90                        95                       100

TGG  AAT  ATT  ACT  GTT  CAG  TGG  TAT  GCT  GGG  GAG  TTC  CTC  TGC  AAA  GTT       390
Trp  Asn  Ile  Thr  Val  Gln  Trp  Tyr  Ala  Gly  Glu  Phe  Leu  Cys  Lys  Val
                    105                       110                       115

CTC  AGC  TAT  CTG  AAG  CTC  TTC  TCT  ATG  TAT  GCC  CCA  GCT  TTC  ATG  ATG       438
Leu  Ser  Tyr  Leu  Lys  Leu  Phe  Ser  Met  Tyr  Ala  Pro  Ala  Phe  Met  Met
               120                       125                       130

GTG  GTG  ATT  AGC  CTG  GAC  CGC  TCC  CTG  GCC  ATC  ACT  CAG  CCC  CTT  GCT       486
Val  Val  Ile  Ser  Leu  Asp  Arg  Ser  Leu  Ala  Ile  Thr  Gln  Pro  Leu  Ala
               135                       140                       145

GTA  CAA  AGC  AAC  AGC  AAG  CTT  GAA  CAG  TCT  ATG  ATC  AGC  CTG  GCC  TGG       534
Val  Gln  Ser  Asn  Ser  Lys  Leu  Glu  Gln  Ser  Met  Ile  Ser  Leu  Ala  Trp
     150                       155                       160

ATT  CTC  AGC  ATT  GTC  TTT  GCA  GGA  CCA  CAG  TTA  TAT  ATC  TTC  AGG  ATG       582
Ile  Leu  Ser  Ile  Val  Phe  Ala  Gly  Pro  Gln  Leu  Tyr  Ile  Phe  Arg  Met
165                       170                       175                       180

ATC  TAC  CTA  GCA  GAC  GGC  TCT  GGG  CCC  ACA  GTC  TTC  TCG  CAA  TGT  GTG       630
Ile  Tyr  Leu  Ala  Asp  Gly  Ser  Gly  Pro  Thr  Val  Phe  Ser  Gln  Cys  Val
                    185                       190                       195

ACC  CAC  TGC  AGC  TTT  CCA  CAG  TGG  TGG  CAT  CAG  GCC  TTC  TAC  AAC  TTT       678
Thr  His  Cys  Ser  Phe  Pro  Gln  Trp  Trp  His  Gln  Ala  Phe  Tyr  Asn  Phe
               200                       205                       210

TTC  ACC  TTC  GGC  TGC  CTC  TTC  ATC  ATC  CCC  CTC  CTC  ATC  ATG  CTA  ATC       726
Phe  Thr  Phe  Gly  Cys  Leu  Phe  Ile  Ile  Pro  Leu  Leu  Ile  Met  Leu  Ile
          215                       220                       225

TGC  AAT  GCC  AAA  ATC  ATC  TTT  GCT  CTC  ACG  CGA  GTC  CTT  CAT  CAA  GAC       774
Cys  Asn  Ala  Lys  Ile  Ile  Phe  Ala  Leu  Thr  Arg  Val  Leu  His  Gln  Asp
     230                       235                       240

CCA  CGC  AAA  CTA  CAG  ATG  AAT  CAG  TCC  AAG  AAT  AAT  ATC  CCA  AGA  GCT       822
Pro  Arg  Lys  Leu  Gln  Met  Asn  Gln  Ser  Lys  Asn  Asn  Ile  Pro  Arg  Ala
245                       250                       255                       260

CGG  CTG  AGA  ACG  CTA  AAG  ATG  ACA  GTC  GCA  TTC  GCT  ACC  TCC  TTT  GTC       870
Arg  Leu  Arg  Thr  Leu  Lys  Met  Thr  Val  Ala  Phe  Ala  Thr  Ser  Phe  Val
                    265                       270                       275

GTC  TGC  TGG  ACT  CCC  TAC  TAT  GTC  CTA  GGC  ATT  TGG  TAC  TGG  TTT  GAT       918
Val  Cys  Trp  Thr  Pro  Tyr  Tyr  Val  Leu  Gly  Ile  Trp  Tyr  Trp  Phe  Asp
               280                       285                       290

CCA  GAA  ATG  TTG  AAC  AGG  GTG  TCA  GAG  CCA  GTG  AAT  CAC  TTT  TTC  TTT       966
Pro  Glu  Met  Leu  Asn  Arg  Val  Ser  Glu  Pro  Val  Asn  His  Phe  Phe  Phe
          295                       300                       305

CTC  TTT  GCT  TTC  CTA  AAC  CCG  TGC  TTC  GAC  CCA  CTC  ATA  TAT  GGG  TAT      1014
Leu  Phe  Ala  Phe  Leu  Asn  Pro  Cys  Phe  Asp  Pro  Leu  Ile  Tyr  Gly  Tyr
     310                       315                       320

TTC  TCT  TTG  TAGTTGGGAG ACTACACAAG AACTCAGATA GAAATAAGGT                           1063
Phe  Ser  Leu
325

AACTAATTGC ACCAATTGAG AATAAACTCA AAGCTTTTGA CACACTTATA TACAAGGCAG                    1123

GGTTTAAGGT TAGATTATCA ACCTTGTTTT TGTACAGAGT TTGTTGTTAG AGCTTCAGAA                    1183

GACCTTCAAA AACAAAAAAA AAAAAAAAA AAAAAAAAA AAAA                                       1227
```

( 2 ) INFORMATION FOR SEQ ID NO:2:

( i ) SEQUENCE CHARACTERISTICS:

(A) LENGTH: 327 amino acids
(B) TYPE: amino acid
(D) TOPOLOGY: unknown (ii) MOLECULE TYPE: protein (xi) SEQUENCE DESCRIPTION: SEQ ID NO:2:

| Met | Ala | Asn | Asn | Ala | Ser | Leu | Glu | Gln | Asp | Pro | Asn | His | Cys | Ser | Ala |
|---|---|---|---|---|---|---|---|---|---|---|---|---|---|---|---|
| 1 | | | | 5 | | | | | 10 | | | | | 15 | |

| Ile | Asn | Asn | Ser | Ile | Pro | Leu | Ile | Gln | Gly | Lys | Leu | Pro | Thr | Leu | Thr |
|---|---|---|---|---|---|---|---|---|---|---|---|---|---|---|---|
| | | | 20 | | | | | 25 | | | | | 30 | | |

| Val | Ser | Gly | Lys | Ile | Arg | Val | Thr | Val | Thr | Phe | Phe | Leu | Phe | Leu | Leu |
|---|---|---|---|---|---|---|---|---|---|---|---|---|---|---|---|
| | | 35 | | | | | 40 | | | | | 45 | | | |

| Ser | Thr | Ala | Phe | Asn | Ala | Ser | Phe | Leu | Leu | Lys | Leu | Gln | Lys | Trp | Thr |
|---|---|---|---|---|---|---|---|---|---|---|---|---|---|---|---|
| | 50 | | | | 55 | | | | | 60 | | | | | |

| Gln | Lys | Arg | Lys | Lys | Gly | Lys | Lys | Leu | Ser | Arg | Met | Lys | Val | Leu | Leu |
|---|---|---|---|---|---|---|---|---|---|---|---|---|---|---|---|
| 65 | | | | | 70 | | | | | 75 | | | | | 80 |

| Lys | His | Leu | Thr | Leu | Ala | Asn | Leu | Leu | Glu | Thr | Leu | Ile | Val | Met | Pro |
|---|---|---|---|---|---|---|---|---|---|---|---|---|---|---|---|
| | | | | 85 | | | | | 90 | | | | | 95 | |

| Leu | Asp | Gly | Met | Trp | Asn | Ile | Thr | Val | Gln | Trp | Tyr | Ala | Gly | Glu | Phe |
|---|---|---|---|---|---|---|---|---|---|---|---|---|---|---|---|
| | | | 100 | | | | | 105 | | | | | 110 | | |

| Leu | Cys | Lys | Val | Leu | Ser | Tyr | Leu | Lys | Leu | Phe | Ser | Met | Tyr | Ala | Pro |
|---|---|---|---|---|---|---|---|---|---|---|---|---|---|---|---|
| | | 115 | | | | | 120 | | | | | 125 | | | |

| Ala | Phe | Met | Met | Val | Val | Ile | Ser | Leu | Asp | Arg | Ser | Leu | Ala | Ile | Thr |
|---|---|---|---|---|---|---|---|---|---|---|---|---|---|---|---|
| | 130 | | | | 135 | | | | | 140 | | | | | |

| Gln | Pro | Leu | Ala | Val | Gln | Ser | Asn | Ser | Lys | Leu | Glu | Gln | Ser | Met | Ile |
|---|---|---|---|---|---|---|---|---|---|---|---|---|---|---|---|
| 145 | | | | | 150 | | | | | 155 | | | | | 160 |

| Ser | Leu | Ala | Trp | Ile | Leu | Ser | Ile | Val | Phe | Ala | Gly | Pro | Gln | Leu | Tyr |
|---|---|---|---|---|---|---|---|---|---|---|---|---|---|---|---|
| | | | | 165 | | | | | 170 | | | | | 175 | |

| Ile | Phe | Arg | Met | Ile | Tyr | Leu | Ala | Asp | Gly | Ser | Gly | Pro | Thr | Val | Phe |
|---|---|---|---|---|---|---|---|---|---|---|---|---|---|---|---|
| | | | 180 | | | | | 185 | | | | | 190 | | |

| Ser | Gln | Cys | Val | Thr | His | Cys | Ser | Phe | Pro | Gln | Trp | Trp | His | Gln | Ala |
|---|---|---|---|---|---|---|---|---|---|---|---|---|---|---|---|
| | | 195 | | | | | 200 | | | | | 205 | | | |

| Phe | Tyr | Asn | Phe | Phe | Thr | Phe | Gly | Cys | Leu | Phe | Ile | Ile | Pro | Leu | Leu |
|---|---|---|---|---|---|---|---|---|---|---|---|---|---|---|---|
| | 210 | | | | 215 | | | | | 220 | | | | | |

| Ile | Met | Leu | Ile | Cys | Asn | Ala | Lys | Ile | Ile | Phe | Ala | Leu | Thr | Arg | Val |
|---|---|---|---|---|---|---|---|---|---|---|---|---|---|---|---|
| 225 | | | | | 230 | | | | | 235 | | | | | 240 |

| Leu | His | Gln | Asp | Pro | Arg | Lys | Leu | Gln | Met | Asn | Gln | Ser | Lys | Asn | Asn |
|---|---|---|---|---|---|---|---|---|---|---|---|---|---|---|---|
| | | | | 245 | | | | | 250 | | | | | 255 | |

| Ile | Pro | Arg | Ala | Arg | Leu | Arg | Thr | Leu | Lys | Met | Thr | Val | Ala | Phe | Ala |
|---|---|---|---|---|---|---|---|---|---|---|---|---|---|---|---|
| | | | 260 | | | | | 265 | | | | | 270 | | |

| Thr | Ser | Phe | Val | Val | Cys | Trp | Thr | Pro | Tyr | Tyr | Val | Leu | Gly | Ile | Trp |
|---|---|---|---|---|---|---|---|---|---|---|---|---|---|---|---|
| | | 275 | | | | | 280 | | | | | 285 | | | |

| Tyr | Trp | Phe | Asp | Pro | Glu | Met | Leu | Asn | Arg | Val | Ser | Glu | Pro | Val | Asn |
|---|---|---|---|---|---|---|---|---|---|---|---|---|---|---|---|
| | 290 | | | | 295 | | | | | 300 | | | | | |

| His | Phe | Phe | Phe | Leu | Phe | Ala | Phe | Leu | Asn | Pro | Cys | Phe | Asp | Pro | Leu |
|---|---|---|---|---|---|---|---|---|---|---|---|---|---|---|---|
| 305 | | | | | 310 | | | | | 315 | | | | | 320 |

| Ile | Tyr | Gly | Tyr | Phe | Ser | Leu |
|---|---|---|---|---|---|---|
| | | | | 325 | | |

(2) INFORMATION FOR SEQ ID NO:3:

(i) SEQUENCE CHARACTERISTICS:
(A) LENGTH: 2160 base pairs
(B) TYPE: nucleic acid
(C) STRANDEDNESS: double
(D) TOPOLOGY: unknown ( i i ) MOLECULE TYPE: DNA (genomic)

( i x ) FEATURE:
    ( A ) NAME/KEY: CDS
    ( B ) LOCATION: 25..1008

( x i ) SEQUENCE DESCRIPTION: SEQ ID NO:3:

```
CGGAGCCTTG TGTCCTGGGA AAAT ATG GCA AAC AGT GCC TCT CCT GAA CAG        51
                          Met Ala Asn Ser Ala Ser Pro Glu Gln
                           1               5

AAT CAA AAT CAC TGT TCA GCC ATC AAC AAC AGC ATC CCA CTG ATG CAG        99
Asn Gln Asn His Cys Ser Ala Ile Asn Asn Ser Ile Pro Leu Met Gln
 10              15                  20                  25

GGC AAC CTC CCC ACT CTG ACC TTG TCT GGA AAG ATC CGA GTG ACG GTT       147
Gly Asn Leu Pro Thr Leu Thr Leu Ser Gly Lys Ile Arg Val Thr Val
         30                  35                  40

ACT TTC TTC CTT TTT CTG CTC TCT GCG ACC TTT AAT GCT TCT TTC TTG       195
Thr Phe Phe Leu Phe Leu Leu Ser Ala Thr Phe Asn Ala Ser Phe Leu
             45                  50                  55

TTG AAA CTT CAG AAG TGG ACA CAG AAG AAA GAG AAA GGG AAA AAG CTC       243
Leu Lys Leu Gln Lys Trp Thr Gln Lys Lys Glu Lys Gly Lys Lys Leu
         60                  65                  70

TCA AGA ATG AAG CTG CTC TTA AAA CAT CTG ACC TTA GCC AAC CTG TTG       291
Ser Arg Met Lys Leu Leu Leu Lys His Leu Thr Leu Ala Asn Leu Leu
     75                  80                  85

GAG ACT CTG ATT GTC ATG CCA CTG GAT GGG ATG TGG AAC ATT ACA GTC       339
Glu Thr Leu Ile Val Met Pro Leu Asp Gly Met Trp Asn Ile Thr Val
 90                  95                 100                 105

CAA TGG TAT GCT GGA GAG TTA CTC TGC AAA GTT CTC AGT TAT CTA AAG       387
Gln Trp Tyr Ala Gly Glu Leu Leu Cys Lys Val Leu Ser Tyr Leu Lys
                110                 115                 120

CTT TTC TCC ATG TAT GCC CCA GCC TTC ATG ATG GTG GTG ATC AGC CTG       435
Leu Phe Ser Met Tyr Ala Pro Ala Phe Met Met Val Val Ile Ser Leu
            125                 130                 135

GAC CGC TCC CTG GCT ATC ACG AGG CCC CTA GCT TTG AAA AGC AAC AGC       483
Asp Arg Ser Leu Ala Ile Thr Arg Pro Leu Ala Leu Lys Ser Asn Ser
        140                 145                 150

AAA GTC GGA CAG TCC ATG GTT GGC CTG GCC TGG ATC CTC AGT AGT GTC       531
Lys Val Gly Gln Ser Met Val Gly Leu Ala Trp Ile Leu Ser Ser Val
    155                 160                 165

TTT GCA GGA CCA CAG TTA TAC ATC TTC AGG ATG ATT CAT CTA GCA GAC       579
Phe Ala Gly Pro Gln Leu Tyr Ile Phe Arg Met Ile His Leu Ala Asp
170                 175                 180                 185

AGC TCT GGA CAG ACA AAA GTT TTC TCT CAA TGT GTA ACA CAC TGC AGT       627
Ser Ser Gly Gln Thr Lys Val Phe Ser Gln Cys Val Thr His Cys Ser
                190                 195                 200

TTT TCA CAA TGG TGG CAT CAA GCA TTT TAT AAC TTT TTC ACC TTC AGC       675
Phe Ser Gln Trp Trp His Gln Ala Phe Tyr Asn Phe Phe Thr Phe Ser
            205                 210                 215

TGC CTC TTC ATC ATC CCT CTT TTC ATC ATG CTG ATC TGC AAT GCA AAA       723
Cys Leu Phe Ile Ile Pro Leu Phe Ile Met Leu Ile Cys Asn Ala Lys
        220                 225                 230

ATC ATC TTC ACC CTG ACA CGG GTC CTT CAT CAG GAC CCC CAC GAA CTA       771
Ile Ile Phe Thr Leu Thr Arg Val Leu His Gln Asp Pro His Glu Leu
    235                 240                 245

CAA CTG AAT CAG TCC AAG AAC AAT ATA CCA AGA GCA CGG CTG AAG ACT       819
Gln Leu Asn Gln Ser Lys Asn Asn Ile Pro Arg Ala Arg Leu Lys Thr
250                 255                 260                 265

CTA AAA ATG ACG GTT GCA TTT GCC ACT TCA TTT ACT GTC TGC TGG ACT       867
Leu Lys Met Thr Val Ala Phe Ala Thr Ser Phe Thr Val Cys Trp Thr
                270                 275                 280
```

|   |   |   |   |   |   |   |   |   |   |   |   |   |   |   |   |   |
|---|---|---|---|---|---|---|---|---|---|---|---|---|---|---|---|---|
| CCC | TAC | TAT | GTC | CTA | GGA | ATT | TGG | TAT | TGG | TTT | GAT | CCT | GAA | ATG | TTA | 915 |
| Pro | Tyr | Tyr | Val | Leu | Gly | Ile | Trp | Tyr | Trp | Phe | Asp | Pro | Glu | Met | Leu |   |
|     |     |     | 285 |     |     |     | 290 |     |     |     |     | 295 |     |     |     |   |
| AAC | AGG | TTG | TCA | GAC | CCA | GTA | AAT | CAC | TTC | TTC | TTT | CTC | TTT | GCC | TTT | 963 |
| Asn | Arg | Leu | Ser | Asp | Pro | Val | Asn | His | Phe | Phe | Phe | Leu | Phe | Ala | Phe |   |
|     |     | 300 |     |     |     |     | 305 |     |     |     |     | 310 |     |     |     |   |
| TTA | AAC | CCA | TGC | TTT | GAT | CCA | CTT | ATC | TAT | GGA | TAT | TTT | TCT | CTG |   | 1008 |
| Leu | Asn | Pro | Cys | Phe | Asp | Pro | Leu | Ile | Tyr | Gly | Tyr | Phe | Ser | Leu |   |   |
|     | 315 |     |     |     |     | 320 |     |     |     |     | 325 |     |     |     |   |   |

```
TGATTGATAG ACTACACAAG AAGTCATATG AAGAAGGGTA AGGTAATGAA TCTCTCCATC    1068
TGGGAATGAT TAACACAAAT GTTGGAGCAT GTTACATAC  AAACAAAGTA GGATTTACAC    1128
TTAAGTTATC ATTCTTTTAG AAACTCAGTC TTCAGAGCCT CAATTATTAA GGAAAAGTCT    1188
TCAGGAAAAA TACTAAAATA TTTTCTCTTC CTCATAAGCT TCTAAATTAA TCTCTGCCTT    1248
TTCTGACCTC ATATAACACA TTATGTAGGT TTCTTATCAC TTTCTCTTTG CATAATAATG    1308
TACTAATATT TAAATACCT  TCAGCCTAAG GCACAAGGAT GCCAAAAAA  CAAAGGTGAG    1368
AACCCACAAC ACAGGTCTAA ACTCAGCATG CTTGGTGAGT TTTTCTCCAA AGGGGCATAT    1428
TAGCAATTAG AGTTGTATGC TATATAATAC ATAGAGCACA GAGCCCTTTG CCCATAATAT    1488
CAACTTTCCC TCCTATAGTT AAAAGAAAA  AAAATGAAT  CTATTTTCT  CTTTGGCTTC    1548
AAAAGCATTC TGACATTGG  AGGAGTCAGT AACCAATCCC ACCAACCACT CCAGCAACCT    1608
GACAAGACTA TGAGTAGTTC TCCTTCATCC TATTTATGTG GTACAGGTTG TGAAGTATCT    1668
CTATATAAAG GGAAATTTTA GAGGGGTTAG GATTGGACA  GGGGTTTAGA ACATTCCTCT    1728
AAGCTATCTA GTCTGTGGAG TTTGTGGCAA TTAATTGCCA TAAAATAACA TGTTTCCAAA    1788
TGCAACTAAG AAAATACTCA TAGTGAGTAC GCTCTATGCA TAGTATGACT TCTATTTAAT    1848
GTGAAGAATT TTTTGTCTCT CTCCTGATCT TACTAAATCC ATATTTCATA AATGAACTGA    1908
GAATAATTAA CAAAATTAAG CAAATGCACA AGCAAAAGAT GCTTGATACA CAAAAGGAAC    1968
TCTGGAGAGA AAACTACAGC TTCAGTCTGT ACAGATCAAA GAAGACAGAA CATGTCAGGG    2028
GAAGGAGGAA AGATCTTGAT GCAGGGTTTC TTAACCTGCA GTCTATGCAC AACACTATAT    2088
TTCCATGTAA TGTTTTATT  TCAGCCCTAT TTGTATTATT TTGTGCATTT AAAAAACACA    2148
ATCTTAAGGC CG                                                        2160
```

( 2 ) INFORMATION FOR SEQ ID NO:4:

( i ) SEQUENCE CHARACTERISTICS:
        ( A ) LENGTH: 328 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

```
Met Ala Asn Ser Ala Ser Pro Glu Gln Asn Gln Asn His Cys Ser Ala
 1               5                  10                  15

Ile Asn Asn Ser Ile Pro Leu Met Gln Gly Asn Leu Pro Thr Leu Thr
                20                  25                  30

Leu Ser Gly Lys Ile Arg Val Thr Val Thr Phe Phe Leu Phe Leu Leu
            35                  40                  45

Ser Ala Thr Phe Asn Ala Ser Phe Leu Leu Lys Leu Gln Lys Trp Thr
        50                  55                  60

Gln Lys Lys Glu Lys Gly Lys Lys Leu Ser Arg Met Lys Leu Leu Leu
65                  70                  75                  80

Lys His Leu Thr Leu Ala Asn Leu Leu Glu Thr Leu Ile Val Met Pro
```

|  |  |  |  | 85 |  |  |  |  | 90 |  |  |  |  | 95 |  |
|---|---|---|---|---|---|---|---|---|---|---|---|---|---|---|---|
| Leu | Asp | Gly | Met 100 | Trp | Asn | Ile | Thr | Val 105 | Gln | Trp | Tyr | Ala | Gly 110 | Glu | Leu |
| Leu | Cys | Lys 115 | Val | Leu | Ser | Tyr | Leu 120 | Lys | Leu | Phe | Ser | Met 125 | Tyr | Ala | Pro |
| Ala | Phe 130 | Met | Met | Val | Val | Ile 135 | Ser | Leu | Asp | Arg | Ser 140 | Leu | Ala | Ile | Thr |
| Arg 145 | Pro | Leu | Ala | Leu | Lys 150 | Ser | Asn | Ser | Lys | Val 155 | Gly | Gln | Ser | Met | Val 160 |
| Gly | Leu | Ala | Trp | Ile 165 | Leu | Ser | Ser | Val | Phe 170 | Ala | Gly | Pro | Gln | Leu 175 | Tyr |
| Ile | Phe | Arg | Met 180 | Ile | His | Leu | Ala | Asp 185 | Ser | Ser | Gly | Gln | Thr 190 | Lys | Val |
| Phe | Ser | Gln 195 | Cys | Val | Thr | His | Cys 200 | Ser | Phe | Ser | Gln | Trp 205 | Trp | His | Gln |
| Ala | Phe 210 | Tyr | Asn | Phe | Phe | Thr 215 | Phe | Ser | Cys | Leu | Phe 220 | Ile | Ile | Pro | Leu |
| Phe 225 | Ile | Met | Leu | Ile | Cys 230 | Asn | Ala | Lys | Ile | Ile 235 | Phe | Thr | Leu | Thr | Arg 240 |
| Val | Leu | His | Gln | Asp 245 | Pro | His | Glu | Leu | Gln 250 | Leu | Asn | Gln | Ser | Lys 255 | Asn |
| Asn | Ile | Pro | Arg 260 | Ala | Arg | Leu | Lys | Thr 265 | Leu | Lys | Met | Thr | Val 270 | Ala | Phe |
| Ala | Thr | Ser 275 | Phe | Thr | Val | Cys | Trp 280 | Thr | Pro | Tyr | Tyr | Val 285 | Leu | Gly | Ile |
| Trp | Tyr 290 | Trp | Phe | Asp | Pro | Glu 295 | Met | Leu | Asn | Arg | Leu 300 | Ser | Asp | Pro | Val |
| Asn 305 | His | Phe | Phe | Phe | Leu 310 | Phe | Ala | Phe | Leu | Asn 315 | Pro | Cys | Phe | Asp | Pro 320 |
| Leu | Ile | Tyr | Gly | Tyr 325 | Phe | Ser | Leu |  |  |  |  |  |  |  |  |

CLONING AND EXPRESSION OF GONADOTROPIN-RELEASING HORMONE RECEPTOR

The present application is a continuation-in-part of co-pending application Ser. No. 07/904,072, filed Jun. 23, 1992, now abandoned which is incorporated by reference herein in its entirety.

This invention was made, in part, with government support under 91-06877 awarded by the NSF. The government has certain rights in the invention.

1. INTRODUCTION

The present invention relates to the cloning of gonadotropin-releasing hormone receptor (GnRH-R), and genetically engineered host cells which express the GnRH-R. Such engineered cells may be used to evaluate and screen drugs and analogs of GnRH involved in GnRH-R activation, regulation and uncoupling.

2. BACKGROUND OF THE INVENTION

The GnRH-R is a key mediator in the integration of the neural and endocrine systems. Normal reproduction depends on the pulsatile release of physiological concentrations of GnRH which binds to specific high affinity pituitary receptors and triggers the secretion of the gonadotropins luteinizing hormone (LH) and follicle stimulating hormone (FSH). Whereas physiological concentrations of GnRH orchestrate normal reproduction, high levels of agonist lead to an opposite response, the suppression of gonadotropin secretion. The capacity of GnRH analogues both to activate and to inhibit the hypothalamic-pituitary-gonadal axis has led to their wide clinical utility in the treatment of a variety of disorders ranging from infertility to prostatic carcinoma.

The responsiveness and capacity of the gonadotrope GnRH-R is influenced by agonist, concentration and pattern of exposure (Clayton, 1989, J Endocrinol 120: 11–19). Both in vivo and in vitro studies have demonstrated that low concentration pulsatile GnRH is trophic to the receptor and that a high concentration of agonist induces receptor down-regulation and desensitization. The binding of GnRH to its receptor stimulates phospholipase C and generates inositol-1,4,5-triphosphate and diacylglycerol (Huckle & Conn, 1988, Endocrine Reviews 9: 387–395). These second messengers, in turn, release calcium from intracellular stores and activate protein kinase C. Receptor up-regulation appears to involve both protein kinase C and calcium (Huckle & Conn, 1988, Endocrine Reviews 9: 387–395; Huckle et al., 1988, Journal of Biological Chemistry 263: 3296–3302; Young et al., 1985, Journal of Endocrinology 107: 49–56). It is not certain which effectors underlie down-regulation.

While great progress has been made in understanding the mechanisms underlying GnRH-R regulation and desensitization through receptor binding studies, direct measurement of GnRH-R gene transcription and biosynthesis has not been possible. Cloning of the GnRH-R cDNA would advance the evaluation of GnRH-R activation, regulation and uncoupling. Determining the primary sequence of the receptor would facilitate the directed design of improved analogues. However, despite intensive interest, heretofore, the GnRH-R gene has not been cloned and expressed in any species.

SUMMARY OF THE INVENTION

The present invention relates to the GnRH-R genes and proteins. The DNA sequences disclosed herein may be engineered into expression systems designed for the production of GnRH-R and/or cell lines which express the GnRH-R and preferably respond to GnRH induced signal transduction. Such cell lines may advantageously be used for screening and identifying GnRH agonists and antagonists. In accordance with another aspect of the invention, the GnRH DNA, antisense oligonucleotide sequences, the GnRH expression products, and antibodies to such products may be used in the diagnosis and therapy of reproductive disorders associated with abnormal expression of the GnRH-R; e.g., overexpression, underexpression or expression of a dysfunctional mutant receptor. Transgenic animals containing the GnRH-R transgene may be used as animal models for the evaluation of GnRH analogs in vivo.

The elucidation of the GnRH-R sequence described herein reflects a major advance in reproductive endocrinology and reveals the complex nature of GnRH-R signal transduction and regulation. Unlike most hormonal signals, GnRH is released in a pulsatile fashion, with the frequency and amplitude of the pulses conveying crucial information (Weiss et al., 1990, Mol. Endocrinol. 4: 557–564; Hasenleder et al., 1991, Endocrinology 128: 509–517). GnRH-R binding capacity itself is either up- or down-regulated by agonists depending on duration of exposure and concentration (Loumaye & Catt, 1982, Science 215: 983–985). The clinical utility of GnRH agonists, which help control a variety of human diseases, including prostatic hypertrophy, prostatic cancer, endometriosis and precocious puberty, depends on this induction of pituitary desensitization. The cloning of the GnRH-R will lead to greater understanding of the complex interplay of hypothalamic, pituitary and gonadal hormones which underlies both pharmacotherapy and reproduction.

4. DESCRIPTION OF THE FIGURES

FIGS. 1A and B Hybrid-arrest of serotonin (5HT) receptor and GnRH-R expression by antisense oligonucleotides. 100 nM 5HT or 200 nM GnRH were introduced into the bath at the horizontal lines. A, Response to 5HT and GnRH in oocytes previously injected with a mixture of rat brain RNA (for the 5HT response), $\alpha$T3-1 RNA (for the GnRH response) and antisense $5HT_{1c}$ receptor oligonucleotide. 16 cells showed identical responses. B, Response to GnRH and 5HT in oocytes previously injected with a mixture of rat brain RNA, $\alpha$T3-1 RNA and antisense WZ7 oligonucleotide. 24 cells had identical responses.

FIGS. 2A and B Characterization of clone WZ25 expressed in oocytes. A, Electrophysiological response to GnRH of oocytes injected with the WZ25 transcript in the absence (left) or presence (right) of GnRH antagonist. The three tracings shown are from different cells. Solid and dotted lines indicate GnRH and GnRH antagonist administration, respectively. Uninjected oocytes had no response to GnRH (n=12). B, Displacement of $^{125}$I-GnRH-A by GnRH-A and GnRH in membranes of oocytes injected with transcript from WZ25. A comparative displacement curve using $\alpha$T3-1 cell membranes combined with membranes from uninjected oocytes is also shown (●). Error bars show SEM.

FIG. 3. Nucleotide (SEQ. ID NO: 1) and deduced amino acid sequences (SEQ. ID NO: 2) of clone WZ25. Numbering begins with the first methionine of the 981 base pair open reading frame. The deduced amino acid sequence is shown below the nucleotide sequence. Putative transmembrane regions I-VII are underlined. Symbols below the amino acid sequences indicate potential N-glycosylation sites (▲), and phosphorylation sites for protein kinase A (♦), Casein kinase 2 (●) and protein kinase C (*)) (Hubbard & Ivatt, 1981, Ann Rev. Biochem. 50: 555–583; Kemp & Pearson, 1990, Trends Biochem. Sci. 15: 342–346; Pearson & Kemp, 1991, Meth. Enzymol. 200: 62–81; Kennelly & Krebs, 1991, J. Biol. Chem. 266: 15555–15558).

Figure 4A:
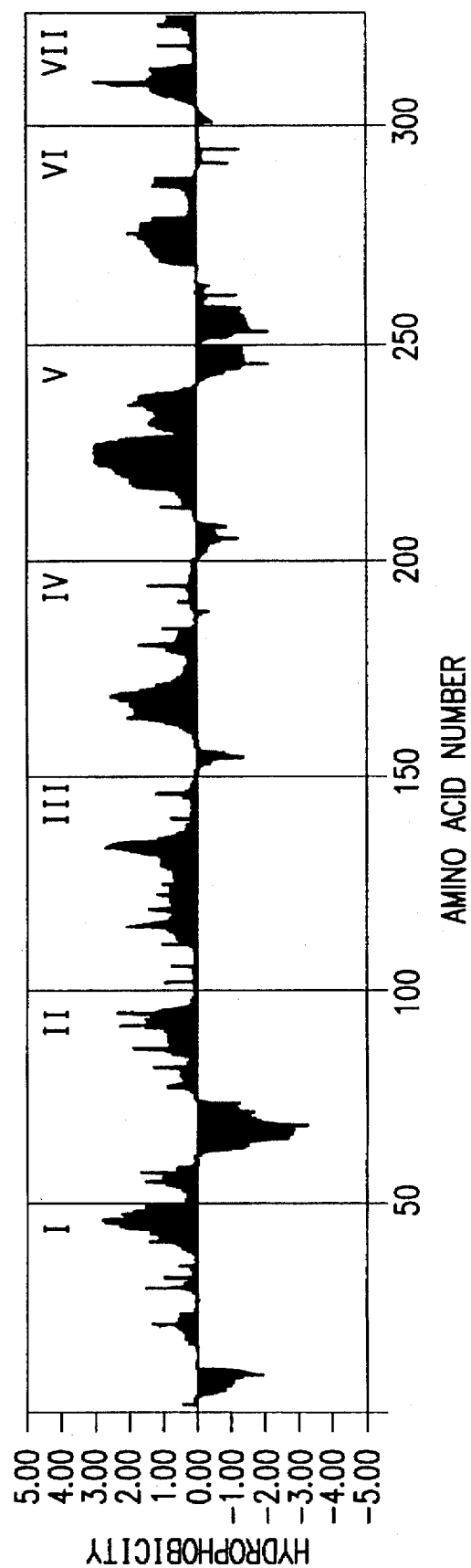

FIG. 4. Hydrophobicity plot of the GnRH-R and amino acid sequence alignment of: GnR, mouse gonadotropin-releasing hormone receptor; ILR, human interleukin-8 receptor.(Murphy & Tiffany, 1991, Science 253: 1280–1283); SPR, rat substance P receptor (Hershey & Krause, 1990, Science 247: 958–962); β1R, human β1-adrenergic (Frielle et al., 1987, Proc. Natl. Acad. Sci. U.S.A. 84: 7920–7924); and RHO, human rhodopsin (Nathans & Hogness, 1984, Proc. Natl. Acad. Sci. U.S.A. 81: 4851–4855). I-VII denote putative transmembrane regions. Boxes indicate identical amino acid residues.

FIGS. 5A–D. Distribution of GnRH-R mRNA.

Autoradiogram of A, solution hybridization assay using 2 μg of total mouse pituitary, GT-1, GH3, and AtT20 RNA and 625 ng of αT3-1 total RNA. B, northern blot analysis with 3 μg of poly(A)+ αT3-1 RNA, and C-F, rat anterior pituitary in situ hybridization. C, antisense probe X-ray film autoradiography. D, sense probe control (calibration bar=450 μm). E,F, dark-field (calibration bar=50 μm), bright-field (calibration bar=100 μm) photomicrographs of emulsion-dipped anterior pituitary section. The molecular weight markers are Hind III digested λ DNA.

Figure 6:
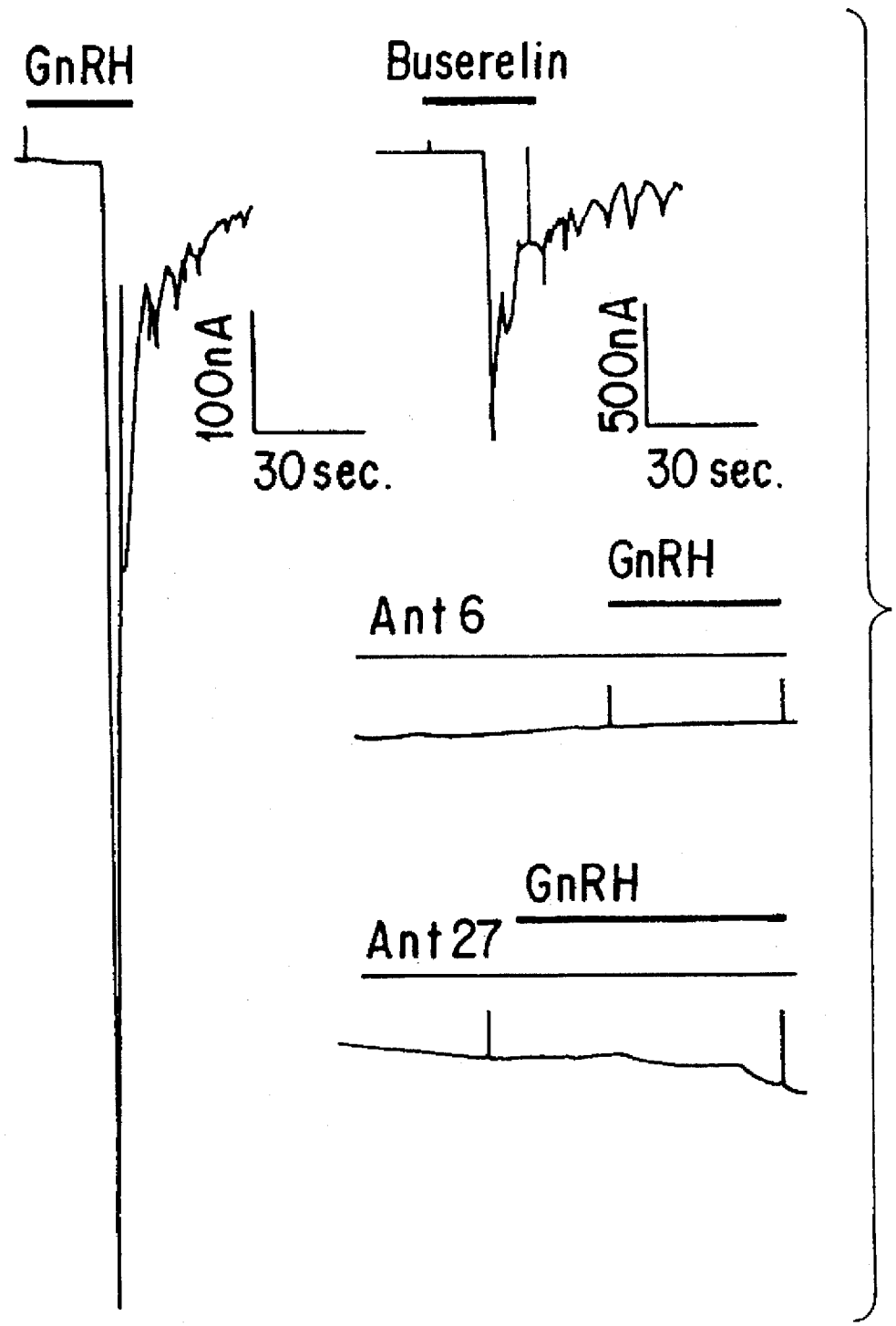

FIG. 6. Expression of the human GnRH-R cDNA in Xenopus oocytes.

Figure 7:
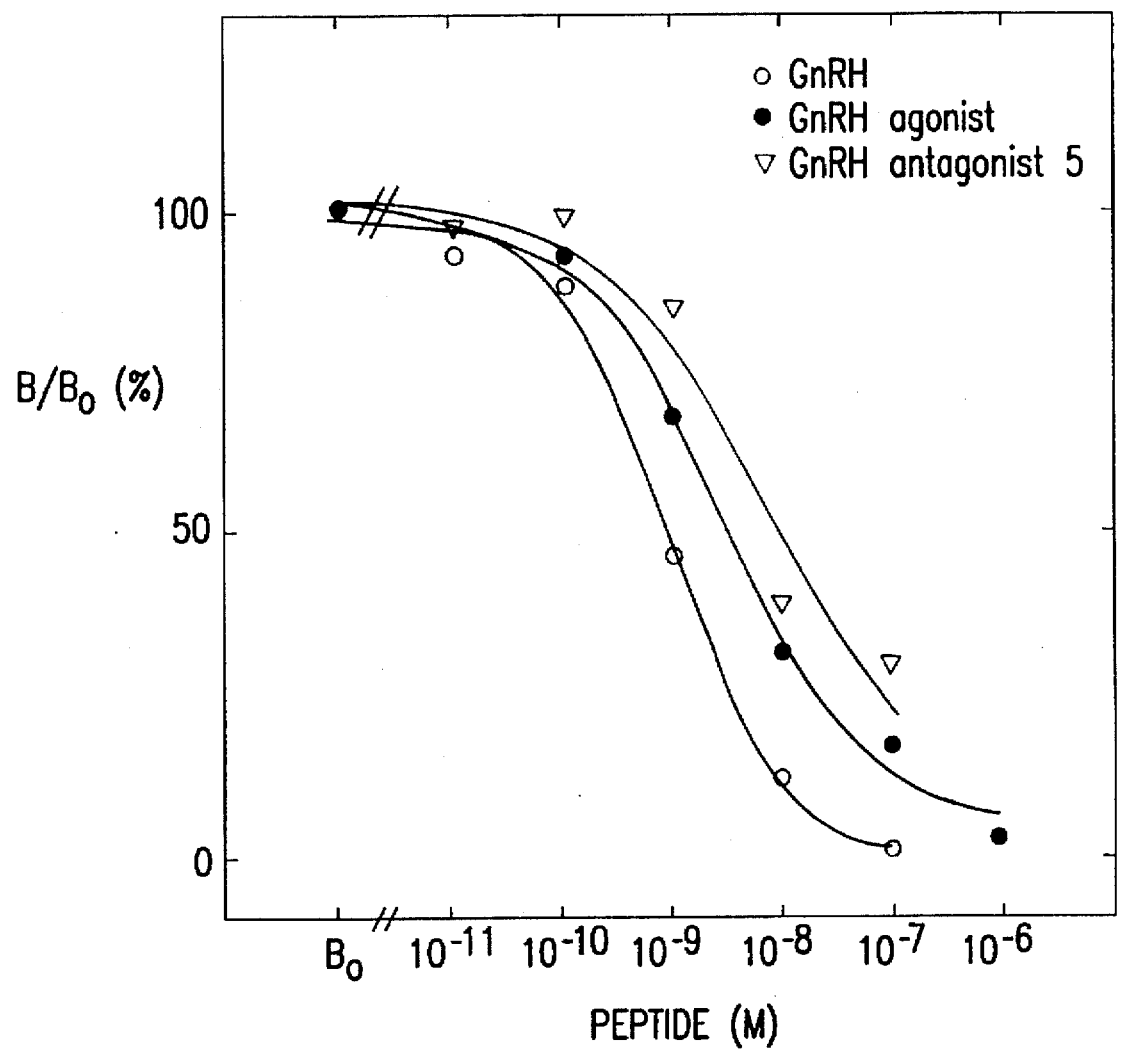

FIG. 7. Displacement of [$^{125}$I]GnRh agonist binding to membranes prepared from COS-1 cells transfected with the pSV2A-human Gn—RHR construct.

Figure 8:
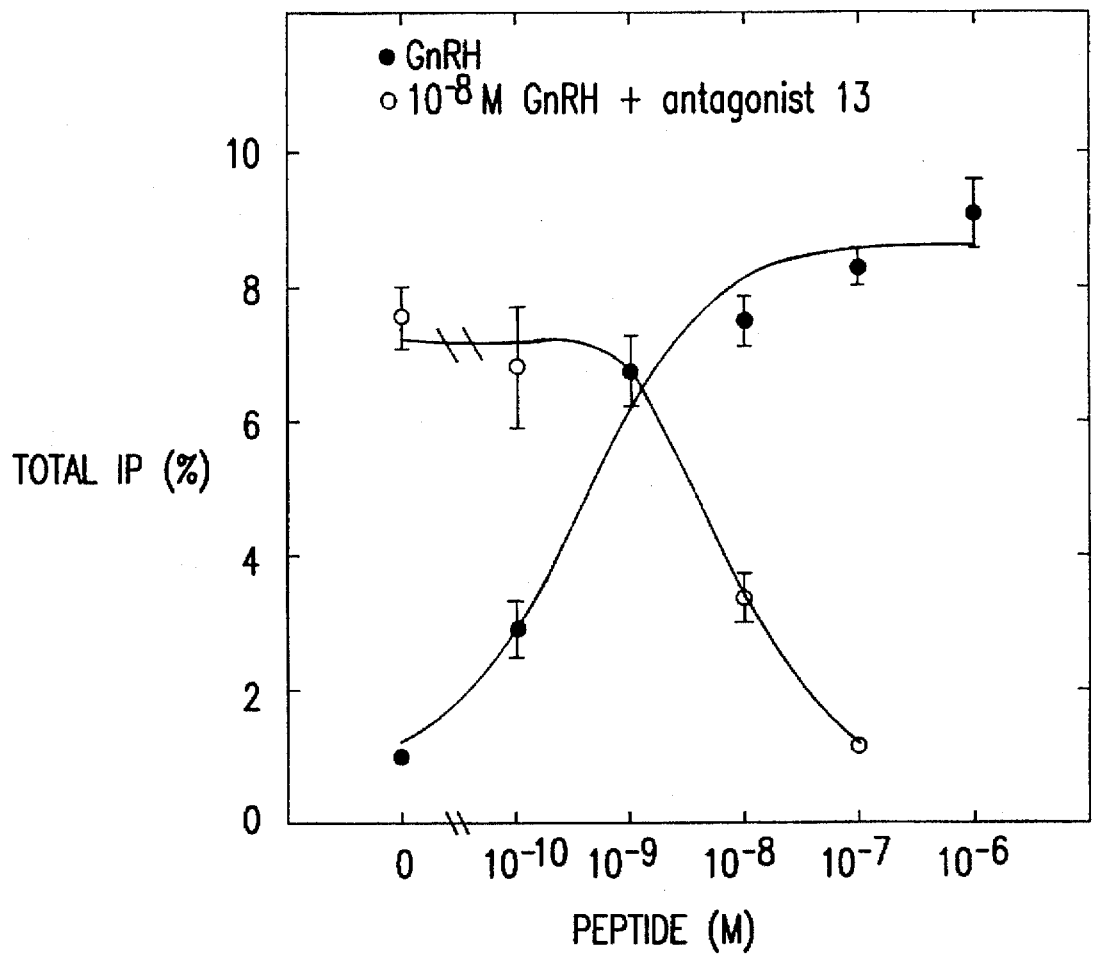

FIG. 8. Effects of GnRH and GnRH antagonist on inositol phosphate production in COS-1 cells transfected with pSV2A-human GnRH-R.

FIG. 9. Nucleotide and putative amino acid sequence of the human GnRH-R.

Figure 10:
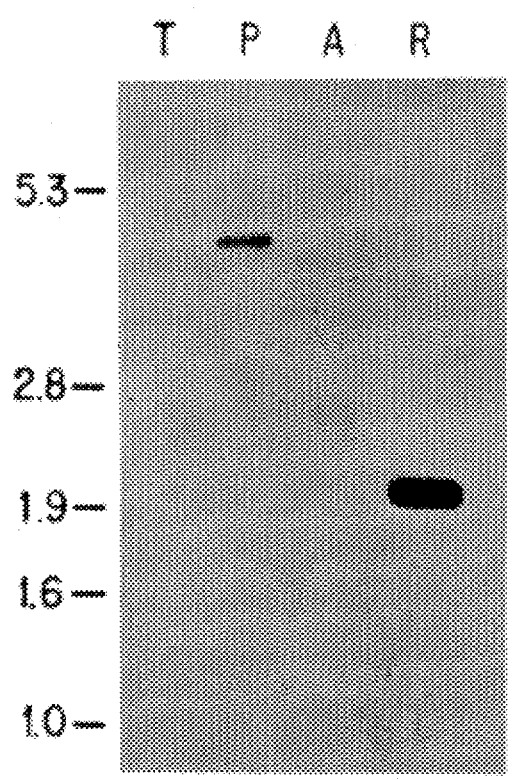

FIG. 10. Northern blot analysis with human GnRH-R cDNA: lane 1 (T): human testis poly(A) RNA; lane 2 (P): human pituitary poly(A) RNA; lane 3 (A): human β-actin cDNA; lane 4 (R): human GnRH-R cDNA.

Figure 11A:
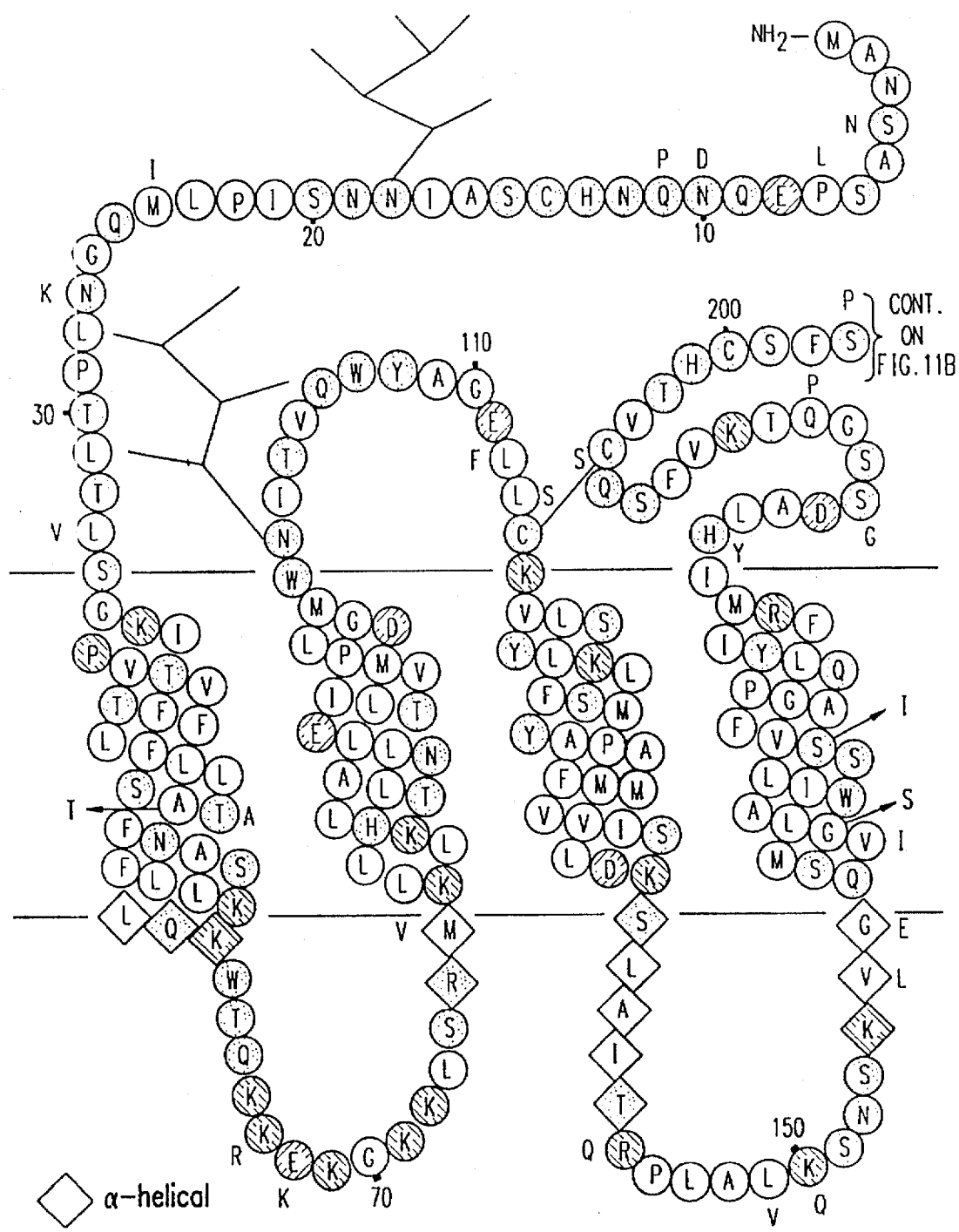
Figure 11B:
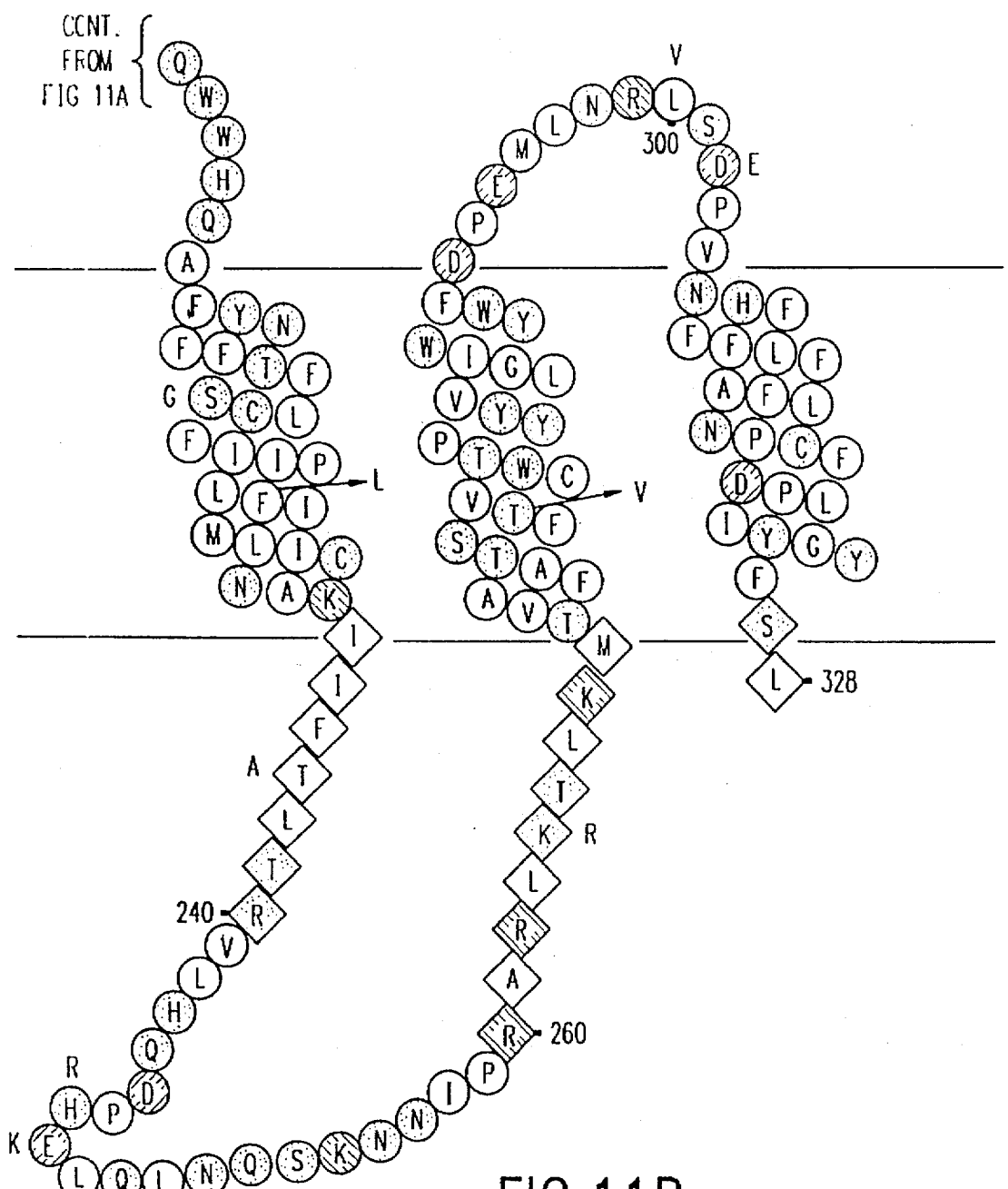

FIG. 11. Schematic of human GnRH-R.

5. DETAILED DESCRIPTION OF THE INVENTION

The present invention relates to the cloning and expression of murine and human GnRH-R. The GnRH-R, which plays a pivotal role in the reproductive system, is characterized by seven transmembrane domains characteristic of G protein-coupled receptors, but lacks a typical intracellular C-terminus. The unusual structure and regulatory domain of the GnRH-R is responsible for the unique aspects of signal transduction and regulation mediated by the receptor. The GnRH-R produced herein may be used to evaluate and screen drugs and analogs of GnRH involved in receptor activation, regulation and uncoupling. Alternatively, GnRH-R DNA, oligonucleotides and/or antisense sequences, or the GnRH-R, peptide fragments thereof, or antibodies thereto may be used in the diagnosis and/or treatment of reproductive disorders.

For clarity of discussion, the invention is described in the subsections below by way of example for the murine and human GnRH-R. However, the principles may be analogously applied to clone and express the GnRH-R of other species, and to clone and express other receptors belonging to the unique GnRH family, i.e., G-protein type of receptors which lack an intracellular C-terminus and bind to GnRH or analogs thereof.

5.1. THE GnRH-R CODING SEQUENCE

The nucleotide coding sequence (SEQ. ID NO: 1) and deduced amino acid sequence (SEQ. ID NO: 2) for the murine GnRH-R are depicted in FIG. 3. The longest open reading frame encodes a 327 amino acid protein of about 37,000 MW. Three consensus N-linked glycosylation sites are present, two in the N-terminus and one in the first extracellular loop (FIG. 3). Hydrophobicity analysis of the deduced protein reveals seven stretches of highly hydrophobic amino acids with 20–30% sequence similarity to other G-protein receptors, with the highest degree of homology to the interleukin-8 receptor (FIG. 4).

The GnRH-R is nearly the smallest member of the G-protein receptor superfamily, the first cytoplasmic loop of the GnRH-R is longer than any other G-protein receptor, and unlike any other G-protein receptor, it lacks a polar cytoplasmic C-terminus. While highly conserved residues are present in the GnRH-R, such as the cysteines in each of the first two extracellular loops which stabilize many receptors, several features of the GnRH-R are unusual. For example, the highly conserved transmembrane II aspartate/glutamate, which has been found to be essential for the function of many G-protein receptors, is replaced by asparagine. Another deviation from other G-protein receptors is the substitution of a serine for the conserved tyrosine located adjacent to transmembrane III. This creates a potential phosphorylation site, unique to the GnRH-R, in a domain critical for signal transduction of other G-protein receptors. Other potential regulatory phosphorylation sites are also present (see FIG. 3).

The invention also relates to GnRH-R genes isolated from other species, including humans. The human GnRH receptor was cloned by probing a λgt10 human pituitary cDNA library with the mouse GnRH receptor insert which had been $^{32}$P-labeled via random hexamer priming. To confirm that the isolated clone encoded a functional human GnRH-R, synthetic RNA transcripts were injected into oocytes. All RNA-injected oocytes developed large depolarizing currents upon exposure to GnRH indicating that the cloned DNA fragment encoded a functional receptor.

The nucleotide coding sequence (SEQ. ID. NO:3) and deduced amino acid sequence (SEQ. ID. NO:4) for the human GnRH-R are depicted in FIG. 9. Sequencing of the human clone identified a 2160 bp insert containing a 984 bp open reading frame. The open reading frame encodes a 328 amino acid protein with 90% identity to the predicted sequence of the mouse receptor.

Hydrophobicity analysis identified the seven hydrophobic domains characteristics of G-protein coupled receptors. As was found for the predicted structure of the mouse receptor, the human GnRH-R lacks essentially any C-terminal intracellular domain. Two potential N-linked glycosylation sites are present, one in each of the first extracellular domains. Several cytoplasmic serine and threonine residues are found on intracellular domains and may serve as regulatory phosphorylation sites (FIG. 11).

Northern blot analysis, utilizing radioactively labelled human GnRH-R as a probe, identified a transcript of roughly 4.7 kb in human pituitary poly(A) RNA (FIG. 10). No signal was detected in poly(A) RNA purified from human testis or with a human β-actin cDNA control.

To determine the extent of the 5' and 3'-untranslated domains of the RNA, PCR analysis of the phage isolates from the primary library screening was undertaken. An antisense oligonucleotide primer representing sequence near the 5'-end of the GnRH-R cDNA insert or a sense primer near the 3'-end of the same sequence was used in conjunction with primers designed against the adjacent GTI-cloning site to map the unpurified clones. The longest PCR products identified had −1.3 kb of additional 5'-sequence and −0.3 kb of additional 3'-sequence. These data suggest that the GnRH-R mRNA contains at least 1.3 kb of 5'-untranslated sequence and 1.5 kb of 3'-untranslated sequence. Based on the Northern blot data, this suggests that additional untranslated sequence (<1 kb) is not contained in any of the clones isolated.

The invention also relates to GnRH-R genes isolated from other species in which GnRH-R activity exists. Members of the GnRH-R family are defined herein as those receptors that bind GnRH. Such receptors may demonstrate about 80% homology at the nucleotide level, and even 90% homology at the amino acid level in substantial stretches of sequences located in regions outside the transmembrane domains.

Cloning of other receptors in the GnRH-R family may be carried out in a number of different ways. For example, the murine and human sequence can be used to design degenerate or fully degenerate oligonucleotide probes which can be used as PCR probes or to screen cDNA libraries derived from appropriate cells which express the GnRH-R, or genomic libraries. The N-terminus and cytoplasmic loops (both intracellular and extracellular) of the murine and human sequences depicted in FIG. 3 and FIG. 11, respectively, may advantageously be used to design such oligonucleotide probes, as these regions should be relatively conserved within the GnRH-R family.

Alternatively, a bacteriophage cDNA library may be screened, under conditions of reduced stringency, sing a radioactively labeled fragment of the human or urine GnRH-R clone to isolate GnRH-R related proteins. For a review of cloning strategies which may be used, see E.g., Maniatis, 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

In accordance with the invention, nucleotide sequences which encode a GnRH-R, fragments, fusion proteins or functional equivalents thereof, may be used to generate recombinant DNA molecules that direct the expression of the GnRH-R, or a functionally active peptide, fusion protein or functional equivalent thereof, in appropriate host cells. Alternatively, nucleotide sequences which hybridize to portions of the GnRH-R sequence may also be used in nucleic acid hybridization assays, Southern and Northern blot analyses, etc.

Due to the degeneracy of the genetic code, other DNA sequences which encode substantially the GnRH-R amino acid sequence, e.g., such as the murine sequence (SEQ. ID NO: 2) depicted in FIG. 3 or the human sequence, or a functional equivalent may be used in the practice of the present invention for the cloning and expression of the GnRH-R. Such DNA sequences include those which are capable of hybridizing to the murine or human GnRH-R sequence under stringent conditions, or which would be capable of hybridizing under stringent conditions but for the degeneracy of the genetic code. The stringency conditions may be adjusted in a number of ways. For example, when performing polymerase chain reactions (PCR), the temperature at which annealing of primers to template takes place or the concentration of $MgCl_2$ in the reaction buffer may be adjusted. When using radioactively labeled DNA fragments or oligonucleotides to probe filters, the stringency may be adjusted by changes in the ionic strength of the wash solutions or by carefully controlling the temperature at which the filter washes are carried out.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the GnRH-R sequence, which result in a silent change thus producing a functionally equivalent GnRH-R. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, aniline; asparagine, glutamine; serine, threonine; phenylalanine, tyrosine. As used herein, a functionally equivalent GnRH-R refers to a receptor which binds to GnRH, but not necessarily with the same binding affinity of its counterpart native GnRH-R.

The DNA sequences of the invention may be engineered in order to alter the GnRH-R coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the GnRH-R coding sequence to eliminate the N-linked glycosylation site; e.g. in the murine sequence this may be accomplished by altering one or more glycosylation sites indicated in FIG. 3. In another embodiment for the invention, the GnRH-R or a modified GnRH-R sequence may be ligated to a heterologous sequence to encode a fusion protein. The fusion protein may be engineered to contain a cleavage site located between the GnRH-R sequence and the heterologous protein sequence, so that the GnRH-R can be cleaved away from the heterologous moiety.

In an alternate embodiment of the invention, the coding sequence of GnRH-R could be synthesized in whole or in part, using chemical methods well known in the art. See, for example, Caruthers, et al., 1980, Nuc. Acids Res. Symp. Ser. 7:215–233; Crea and Horn, 180, Nuc. Acids Res. 9(10):2331; Matteucci and Caruthers, 1980; Tetrahedron Letters 21:719; and Chow and Kempe, 1981, Nuc. Acids Res. 9(12):2807–2817. Alternatively, the protein itself could be produced using chemical methods to synthesize the GnRH-R amino acid sequence in whole or in part. For example, peptides can be synthesized by solid phase techniques, cleaved from the resin, and purified by preparative high performance liquid chromatography. (E.q., see Creighton, 1983, Proteins Structures And Molecular Principles, W. H. Freeman and Co., New York pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., New York, pp. 34–49).

5.2. EXPRESSION OF THE GnRH-R

In order to express a biologically active GnRH-R, the nucleotide sequence coding for GnRH-R, or a functional equivalent as described in Section 5.1 supra, is inserted into an appropriate expression vector, i.e., a vector which contains the necessary elements for the transcription and translation of the inserted coding sequence. The GnRH-R gene products as well as host cells or cell lines transfected or transformed with recombinant GnRH-R expression vectors can be used for a variety of purposes. These include but are not limited to generating antibodies (i.e., monoclonal or polyclonal) that bind to the receptor, including those that competitively inhibit GnRH binding and "neutralize" GnRH activity; the screening and selection of GnRH analogs or drugs that act via the GnRH-R; etc.

5.2.1. EXPRESSION SYSTEMS

Methods which are well known to those skilled in the art can be used to construct expression vectors containing the GnRH-R coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning Laboratory Manual, Cold Spring Harbor Laboratory, New York and Ausubel et al., 1989, Current Protocols in Molecular Biology, Greene Publishing Associates and Wiley Interscience, New York.

A variety of host-expression vector systems may be utilized to express the GnRH-R coding sequence. These include but are not limited to microorganisms such as bacteria transformed with recombinant bacteriophage DNA, plasmid DNA or cosmid DNA expression vectors containing the GnRH-R coding sequence; yeast transformed with recombinant yeast expression vectors containing the GnRH-R coding sequence; insect cell systems infected with recombinant virus expression vectors (e.g., baculovirus) containing the GnRH-R coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the GnRH-R coding sequence; or animal cell systems infected with recombinant virus expression vectors (e.g., adenovirus, vaccinia virus) including cell lines engineered to contain multiple copies of the GnRH-R DNA either stably amplified (e.g., CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the GnRH-R DNA SV40-, BPV- and EBV-based vectors may be used with an appropriate selectable marker.

In bacterial systems a number of expression vectors may be advantageously selected depending upon the use intended for the GnRH-R expressed. For example, when large quantities of GnRH-R are to be produced for the generation of antibodies, vectors which direct the expression of high levels of fusion protein products that are readily purified may be desirable. Such vectors include but are not limited to the *E. coli* expression vector pUR278 (Ruther et al., 1983, EMBO J. 2:1791), in which the GnRH-R coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, New York, Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, New York, Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the GnRH-R coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, New York, Section VIII, pp. 421–463; and Grierson & Corey, 1988, Plant Molecular Biology, 2d Ed., Blackie, London, Ch. 7–9.

An alternative expression system which could be used to express GnRH-R is an insect system. In one such system, *Autographa californica* nuclear polyhidrosis virus (AcNPV)

is used as a vector to express foreign genes. The virus grows in *Spodoptera frugiperda* cells. The GnRH-R coding sequence may be cloned into non-essential regions (for example the polyhedrin gene) of the virus and placed under control of an AcNPV promoter (for example the polyhedrin promoter). Successful insertion of the GnRH-R coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the GnRH-R coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing GnRH-R in infected hosts. (E.g., See Logan & Shenk, 1984, Proc. Natl. Acad. Sci. (U.S.A.) 81:3655–3659). Alternatively, the vaccinia 7.5K promoter may be used. (E.g., see Mackett et al., 1982, Proc. Natl. Acad. Sci. (U.S.A.) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted GnRH-R coding sequences. These signals include the ATG initiation codon and adjacent sequences. In cases where the entire GnRH-R gene, including its own initiation codon and adjacent sequences, is inserted into the appropriate expression vector, no additional translational control signals may be needed. However, in cases where only a portion of the GnRH-R coding sequence is inserted, exogenous translational control signals, including the ATG initiation codon, must be provided. Furthermore, the initiation codon must be in phase with the reading frame of the GnRH-R coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the GnRH-R may be engineered. Rather than using expression vectors which contain viral origins of replication, host cells can be transformed with the GnRH-R DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the GnRH-R on the cell surface, and which respond to GnRH mediated signal transduction. Such engineered cell lines are particularly useful in screening GnRH analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. U.S.A. 48:2026), and adenine phosphoribosyltransferase (Lowy, et al., 1980, Cell 22:817) genes can be employed in tk, hgprt or aprt cells, respectively. Also, antimetabolite resistance can be used as the basis of selection for dhfr, which confers resistance to methotrexate (Wigler, et al., 1980, Natl. Acad. Sci. U.S.A. 77:3567; O'Hare, et al., 1981, Proc. Natl. Acad. Sci. U.S.A. 78:1527); gpt, which confers resistance to mycophenolic acid (Mulligan & Berg, 1981), Proc. Natl. Acad. Sci. U.S.A. 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. U.S.A. 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

In a specific embodiment, described herein, the human GnRH-R cDNA was subcloned into an expression vector, pSV2A, containing the SV40 early promoter. COS-1 cells were transiently transfected with the pSV2A-human GnRH-R construct using the DEAE-dextran method of transfection (Keown, W. A. et al., 1990, in Methods of Enzymology, Vl. 185 (Goeddel, D. V., ed.) pg. 527–537 Academic Press, New York). Experiments, using membranes from COS-1 transfected cells, indicated that the heterologously expressed receptor was capable of binding GnRH. Ligand binding was also found to be coupled to inositol phosphate metabolism indicating further that the transfected COS-1 cells expressed a functional human GnRH-R.

5.2.2. IDENTIFICATION OF TRANSFECTANTS OR TRANSFORMANTS THAT EXPRESS THE GnRH-R

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of GnRH-R mRNA transcripts in the host cell; and (d) detection of the gene product as measured by immunoassay or by its biological activity.

In the first approach, the presence of the GnRH-R coding sequence inserted in the expression vector can be detected by DNA-DNA or DNA-RNA hybridization using probes comprising nucleotide sequences that are homologous to the GnRH-R coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the GnRH-R coding sequence is inserted within a marker gene sequence of the vector, recombinants containing the GnRH-R coding sequence can be identified by the absence of the marker gene function. Alternatively, a marker gene can be placed in tandem with the GnRH-R sequence under the control of the same or different promoter used to control the expression of the GnRH-R coding sequence. Expression of the marker in response to induction or selection indicates expression of the GnRH-R coding sequence.

In the third approach, transcriptional activity for the GnRH-R coding region can be assessed by hybridization assays. For example, RNA can be isolated and analyzed by Northern blot using a probe homologous to the GnRH-R coding sequence or particular portions thereof. Alternatively, total nucleic acids of the host cell may be extracted and assayed for hybridization to such probes.

In the fourth approach, the expression of the GnRH-R protein product can be assessed immunologically, for example by Western blots, immunoassays such as radioimmuno-precipitation, enzyme-linked immunoassays and the like. The ultimate test of the success of the expression system, however, involves the detection of the biologically active GnRH-R gene product. A number of assays can be used to detect receptor activity including but not limited to GnRH binding assays; and GnRH biological assays using engineered cell lines as the test substrate.

In a specific embodiment described herein, cell membranes were prepared from COS-1 cells transfected with a recombinant expression vector containing the human GnRH-R cDNA. Expression of the human GnRH-R was detected using a $^{125}I$ labeled GnRH analog. In addition the expression of biologically active GnRH-R could be detected in transfected cells by measuring levels of GnRH-stimulated inositol phosphate (IP) production as described in Section 7.1.5.

5.2.3. RECOVERY OF THE GnRH-R

Once a clone that produces high levels of biologically active GnRH-R is identified, the clone may be expanded and used to produce large amounts of the receptor which may be purified using techniques well-known in the art including, but not limited to immunoaffinity purification, chromatographic methods including high performance liquid chromatography, affinity chromatography using immobilized ligand such as GnRH or analogs thereof bound to beads, immunoaffinity purification using antibodies and the like.

Where the GnRH-R coding sequence is engineered to encode a cleavable fusion protein, purification may be readily accomplished using affinity purification techniques. For example, a collagenase cleavage recognition consensus sequence may be engineered between the carboxy terminus of GnRH-R and protein A. The resulting fusion protein may be readily purified using an IgG column that binds the protein A moiety. Unfused GnRH-R may be readily released from the column by treatment with collagenase. Another example would be the use of pGEX vectors that express foreign polypeptides as fusion proteins with glutathionine S-transferase (GST). The fusion protein may be engineered with either thrombin or factor Xa cleavage sites between the cloned gene and the GST moiety. The fusion protein may be easily purified from cell extracts by adsorption to glutathione agarose beads followed by elution in the presence of glutathione. In this aspect of the invention, any cleavage site or enzyme cleavage substrate may be engineered between the GnRH-R sequence and a second peptide or protein that has a binding partner which could be used for purification, e.g., any antigen for which an immunoaffinity column can be prepared.

5.3. GENERATION OF ANTIBODIES THAT DEFINE THE GnRH-R

Various procedures known in the art may be used for the production of antibodies to epitopes of the recombinantly produced GnRH-R. Neutralizing antibodies i.e., those which compete for the GnRH binding site of the receptor are especially preferred for diagnostics and therapeutics. Antibodies which define viral serological markers would be preferred for diagnostic uses. Such antibodies include but are not limited to polyclonal, monoclonal, chimeric, single chain, Fab fragments and fragments produced by an Fab expression library.

For the production of antibodies, various host animals may be immunized by injection with the GnRH-R including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and corynebacterium parvum.

Monoclonal antibodies to GnRH-R may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983; Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946, 778) can be adapted to produce GnRH-R-specific single chain antibodies.

Antibody fragments which contain specific binding sites of GnRH-R may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to GnRH-R.

5.4. USES OF THE GnRH-R, DNA AND ENGINEERED CELL LINES

The GnRH-R DNA, antisense oligonucleotides, GnRH-R expression products, antibodies and engineered cell lines described above have a number of uses for the diagnosis and treatment of reproductive disorders and in drug design and discovery.

For example, the GnRH-R DNA sequence may be used in hybridization assays of biopsies to diagnose abnormalities of GnRH-R expression; e.g., Southern or Northern analysis, including in situ hybridization assays. In therapeutic applications, antisense or ribozyme molecules designed on the basis of the GnRH-R DNA sequence may be utilized to block transportation and expression of the GnRH-R gene product. In this regard, oligonucleotides derived from the translation initiation site, e.g., between −10 and +10 regions of the GnRH-R nucleotide sequence, are preferred. Alternatively, the GnRH-R DNA could be used in gene therapy approach to introduce the normal recombinant gene into the defective cells of an individual or to correct an endogenous mutation in order to reconstitute the GnRH-R and its function.

In another embodiment of the invention, antibodies specific for the GnRH-R may be used to determine the pattern of receptor expression in biopsy tissue, or for diagnostic imaging in vivo; in such applications, "neutralizing" antibodies may be preferred. For example, an antibody conjugated to an imaging compound could be administered to a patient to "map" the locations and distribution of the GnRH-R in vivo.

In another embodiment of the invention, the GnRH-R itself, or a fragment containing its GnRH binding site, could be administered in vivo. The free GnRH-R or the peptide fragment could competitively bind to GnRH and inhibit its interaction with the native receptor in vivo.

In another embodiment of the invention, stimulation of an antibody response, specific for GnRH-R, may be used as a means of contraception. For example, various host animals may be immunized by injection with GnRH-R or GnRH-R fusion protein, leading to stimulation of their immune system and production of circulating anti-GnRH-R antibodies.

In yet another embodiment, the engineered cell lines which express the GnRH-R and respond to signal transduction may be utilized to screen and identify biologically active GnRH analogs, i.e., either agonists or antagonists. Transgenic animals which contain the GnRH-R DNA as the transgene may be engineered to test the effects of such agonists or antagonists in vivo.

Recently, computer generated models for ligand-receptor interactions have been developed and in a specific embodiment of the invention information derived from computer modeling of GnRH-R may be used for design of receptor agonist or antagonist. Over 74 distinct GPR (G-protein receptors) sequences have been published and sequence alignments with GnRH-R sequences may facilitate understanding the role of certain protein sequences in determining ligand binding and regulation. Changes made to GnRH-R sequences, using for example techniques for site directed mutagenesis, and expression of mutant receptors in cell lines may be used to further define the functional role of particular receptor regions and residues.

6. EXAMPLE:

CLONING OF A FUNCTIONAL MURINE GnRH-R

The subsections below describe the cloning of a complementary DNA representing the mouse GnRH-R and confirm its identity using *Xenopus oocyte* expression. Injection of sense RNA transcript leads to the expression of a functional, high-affinity GnRH-R. Expression of the GnRH-R using gonadotrope cell line RNA, however, is blocked by an antisense oligonucleotide. In situ hybridization in the rat anterior pituitary reveals a characteristic GnRH-R distribution. The nucleotide sequence encodes a 327 amino acid protein which has the seven putative transmembrane domains characteristic of G protein-coupled receptors, but which lacks a typical intracellular C-terminus. The unusual structure and novel potential regulatory domain of the GnRH-R may explain unique aspects of its signal transduction and regulation.

6.1. MATERIALS AND METHODS

Drugs were obtained from the following sources: the GnRH antagonist [D-Phe$^{2,6}$, Pro$^3$]-GnRH (Bachem, Torrance, Calif.), buserelin (D-Ser(But)$^6$, Pro$^9$-N-ethylamide GnRH) Hoerchst-Roussel Pharmaceuticals (Somerville, N.J.). All other chemicals were from Sigma Chemical Co. (St. Louis, Mo.). All animal care was in accordance with the NIH Guide for the Care and Use of Laboratory Animals.

6.1.1. OOCYTE MICRO-INJECTION AND RECORDING

Adult female *Xenopus laevis* (Nasco, Ft. Atkinson, Wis.) were kept at 18°–20° C. and a day/night cycle of 15 h/9 h. Oocytes were prepared for injection and the responses recorded as previously described (Sealfon et al., 1990, Mol. Endocrinol 4: 119–124). Cells were placed in a 0.5 ml bath and voltage clamped at −70 mV using standard two electrode technique (Dascal, 1987, CRC Crit. Rev. Biochem. 417: 47–61). Peptide ligands were diluted in the perfusion buffer and introduced into the bath. The clamp current was recorded using a chart recorder. Reversal potentials were determined by continuous ramping from −70 to +10 mV over 2 seconds with and without agonist through an IBM PC/AT system using the TL-1 interface and pCLAMP software from Axon Instruments (Burlingame, Calif.).

6.1.2. PCR CLONING AND HYBRID ARREST SCREENING

RNA preparation and cDNA synthesis were performed as previously described (Sealfon et al., 1990, Mol. Endocrinol 4: 119–124; Snyder et al., 1991; Neurosci Lett 122: 37–40). Subclones for hybrid arrest screening were isolated using PCR with a variety of degenerate oligonucleotides corresponding to conserved transmembrane domains of the GPR superfamily. The oligonucleotides used to isolate the group of subclones including WZ7, modified from sequences of published oligomers (Zhou et al., 1990, Nature 347: 76–80), corresponded to transmembrane III (5'-GAGTCGACCTGTG(CT)G(CT) (GC)AT(CT)(AG)CNNT (GT)GAC(AC)G(C G)TAC-3') and transmembrane VI (5'-

CAGAATTCAG(AT)AGGGCANCCAGCAGAN (CG) (AG)(CT)GAA-3'). PCR was performed at low stringency. A portion of the reaction was reamplified at high stringency, digested with restriction enzymes, subcloned into pBluescript II KS+ (Stratagene) and sequenced. For hybrid-arrest assay, an antisense oligonucleotide corresponding to transmembrane II of the $5HT_{1c}$ receptor (5'-ATCAGCAATGGCTAG-3') (Julius et al., 1988, Science 241: 558–564) and an oligonucleotide corresponding to WZ7 (5'-AGCATGATGAGGAGG-3') were synthesized. A mixture of αT3-1 (1 mg/ml) and rat brain total RNA (1 mg/ml) was preincubated with antisense, oligonucleotide (100 µg/ml) for 10 minutes at 37° C. in a buffer containing 200 mM NaCl and 5 mM Tris, pH 7.4 in a 3 µl volume. Xenopus oocytes were injected with 50 nl of the mixture and incubated for 48 hours before recording.

6.1.3. LIBRARY SCREENING AND SEQUENCING $10^6$ plaques of a UniZap (Stratagene) αT3-1 cDNA library were screened with the insert of WZ7 which had been $^{32}$P-labelled by random hexamer primers. 40 positive plaques were identified and 7 purified on secondary and tertiary screening. WZ25 was subcloned into pBluescript II SK+ by helper phage excision and both strands sequenced by the dideoxy-chain termination method with Sequenase T7 DNA polymerase (USB). Sequence was further confirmed by resequencing both strands using taq polymerase labelling and an Applied Biosystems automated sequencer. To exclude the possibility that the predicted cytoplasmic C-terminus was truncated due to a mutation in WZ25, the 3' sequence was confirmed in two additional independent clones. The nucleotide and amino acid sequence were analyzed using the Wisconsin GCG package on a VAX computer and MacVector (IBI) on a microprocessor.

6.1.4. CHARACTERIZATION OF WZ25RNA TRANSCRIPT

WZ25 in pBluescript II SK+ (Stratagene) was linearized and capped RNA transcript synthesized using T3 RNA polymerase (Stratagene). Oocytes were injected with 1.25 ng of the resulting transcript and incubated for 48 hours before recording. Oocytes were pre-treated with either buffer or a GnRH antagonist (antagonist 6: [Ac-D-Nal(2)$^1$,D,α-Me-pCl-Phe$^2$,D-Trp$^3$,D-Arg$^6$, D-Ala$^{10}$]GnRH; antagonist 27: [Ac-D-Nal(2)$^1$,D-α-Me-pCl-Phe$^2$,D-Trp$^3$,N-ε-lpr-Lys$^5$,D-Tyr$^6$,D-Ala$^{10}$]GnRH; ref. (Can der Spuy et al., 1987, In: Vickery BH and Nestor JJ (eds) LHRH and its Analogs: Contraceptive and Therapeutic Applications. NTP Press, Lancaster, England) for 3 minutes prior to GnRH administration. To confirm receptor expression, oocytes were re-exposed to GnRH after a three minute washout of antagonist.

6.1.5. RADIOLIGAND BINDING ASSAY

For membrane preparation, 500 oocytes were each injected with 2.5 ng synthetic WZ25 RNA. After 48 hours, oocyte membranes were prepared as described (Kobilka et al., 1987, J. Biol. Chem. 262: 15796–15802) and resuspended in binding buffer containing 10 mM HEPES, 1 mM EDTA, and 0.1% bovine serum albumin to give a final concentration of 20 oocytes/ml. The receptor binding assay using $^{125}$I-[D-Ala$^6$, NaMe-Leu$^7$, Pro$^9$-NHEt]GnRH (GnRH-A) was based on that previously described for rat and sheep pituitary membranes (Millar et al., 1989, J. Biol. Chem. 264: 21007–21013). The binding in the presence of $10^{-6}$M GnRH analogue was considered to represent non-specific binding. Average Bo (maximal binding) and non-specific binding values were 1429 and 662 cpm, respectively. The dissociation constant (Kd) for GnRH-A and GnRH was determined using Enzfitter (Elsevier-BIOSOFT).

6.1.6. SOLUTION HYBRIDIZATION, NORTHERN BLOT ANALYSIS, AND IN SITU HYBRIDIZATION

A 399 nucleotide $^{32}$P-labelled GnRH-R and a 117 nucleotide 1B15 (cyclophilin internal standard) antisense cRNA probe were synthesized and hybridized to RNA in solution using described methods (Autelitano et al., 1989, Mol. Cell. Endo. 67: 101–105). Northern blot analysis using poly(A)$^+$ αT3-1 RNA was performed as described (Sambrook et al., 1989, Molecular Cloning: A Laboratory Manual. Cold Spring Harbor Laboratory Press, Cold Spring Harbor, N.Y.). In situ hybridization using $^{35}$S-UTP labeled CRNA was performed on free-floating pituitary sections following published methods (Gall & Isackson, 1989, Science 245: 758–761). Sections were mounted and exposed to Amersham Beta-max film for 3 days or dipped in radioactive emulsion and developed after 17 days.

6.2. RESULTS

6.2.1. cDNA CLONING OF A FUNCTIONAL MURINE GnRH-R

RNA from the mouse gonadotrope cell line, αT3-1[5], which directs the expression of a functional GnRH-R in Xenopus oocytes (Sealfon et al., 1990, Mol. Endocrinol 4: 119–124), was used to synthesize cDNA for PCR with degenerate oligonucleotides corresponding to conserved motifs of the G protein-coupled receptors (GPRs; see Probst et al., 1992, DNA and Cell Biol. 11: 1–20). PCR products were subcloned and sequenced, and antisense oligomers synthesized for a hybrid-arrest assay (Kawashi, 1985, Nuc. Acids Res. 13: 4991–5004). An oligonucleotide corresponding to clone WZ7, when co-injected with α-T3-1 and rat brain RNA, completely abolished the expression of the GnRH-R in oocytes but did not affect expression of the brain $5HT_{1c}$ receptor (FIG. 1). A second antisense oligonucleotide, representing a different segment of WZ7, also completely and specifically eliminated GnRH-R expression in all oocytes tested (n=16). Clone WZ7 was used as a probe to screen an αT3-1 bacteriophage cDNA library and seven positive plaques were purified.

To test whether the clone with the largest insert of 1.3 kb, WZ25, encodes a functional GnRH-R, it was subcloned for RNA synthesis and oocyte expression. All synthetic RNA-injected oocytes (n>50), when exposed to GnRH, demonstrated a large depolarizing response characteristic of GnRH-R expression (FIG. 2). The reversal potential (V$_r$) and calcium-dependence of the response to GnRH induced in oocytes by WZ25 RNA transcript were similar to those previously obtained using αT3-1 RNA (Sealfon et al., 1990, Mol. Endocrinol 4: 119–124). The V$_r$ of the current elicited by GnRH was −27±0.79 mV (n=7), consistent with that of the chloride ion in oocytes (Barish, 1983, J. Physiol. 342: 309–325). The GnRH-elicited response was completely abolished by preloading the oocyte with 5 mM EGTA one hour before recording (n=4), but was not significantly affected by the absence of Ca$^{2+}$ in the perfusate (n=7). Thus the receptor expressed from clone WZ25 exhibited a response mediated through the activation of the oocyte's calcium-dependent chloride current by intracellular calcium, as is characteristic of receptors that cause phosphatidylinositol hydrolysis (see Dascal, 1987, CRC Crit. Rev. Biochem. 417: 47–61). The pharmacology of the response obtained was in agreement with expression of the mammalian GnRH-R. The GnRH agonist [D-Ser(t-Bu)$^6$,Pro$^9$-NHEt]GnRH (100 nM buserelin, n=6) elicited a depolarizing current in RNA-injected oocytes. In the presence of equimolar weak GnRH antagonist [D-Phe$^{2,6}$, Pro$^3$]GnRH, there was a 60% reduction in the response to GnRH, in comparison with the response to GnRH alone (1880±551 nA, n=5, and 4756±1082 nA, n=4, respectively). Two potent GnRH antagonists completely eliminated the GnRH-elicited current (FIG. 2A).

Figure 2B:
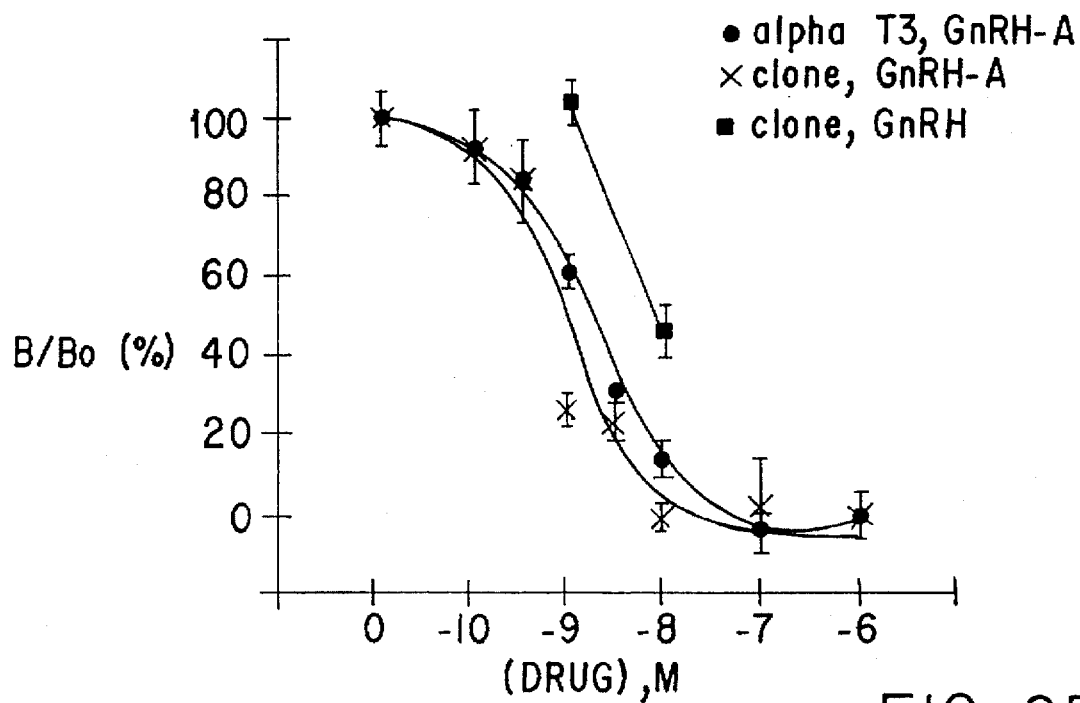

To further characterize the receptor encoded by this cDNA clone, radioligand binding assays were performed on membranes purified from oocytes injected with the WZ25 RNA transcript. The GnRH agonist [D-Ala$^6$, NαMe-Leu$^7$, Pro$^9$-NHEt]GnRH (GnRH-A) bound with high affinity to membranes of oocytes injected with synthetic RNA (FIG. 2B). Displacement of $^{125}$I-GnRH-A by GnRH-A revealed similar Kds of 4.5 and 2.9 nM in WZ25 RNA-injected oocyte membranes and αT3-1 cell membranes respectively. Displacement by GnRH of GnRH-A bound to the cloned receptor was an order of magnitude less effective, as has been previously reported for αT3-1 membranes (Horn et al., 1991, Mol. Endocrinol. 5: 347–355). Thus the hybrid-arrest and expression data confirm that clone WZ25 represents the mouse GnRH-R.

6.2.2. CHARACTERIZATION OF THE CODING SEQUENCE OF MURINE GnRH-R

The nucleotide (SEQ. ID NO: 1) and corresponding predicted amino acid sequence (SEQ. ID NO: 2) of clone WZ25 are shown in FIG. 3. The longest open reading frame encodes a 327 amino acid protein (relative molecular mass, $M_r$=37,683). The larger size reported for the binding subunit of the solubilized rat GnRH-R, $M_r$50,000–60,000 (Hazum et al., 1986, J. Biol. Chem. 261: 13043–13048; Iwashita et al., 1988, J. Mol. Endocrinol. 1: 187–196), may be due to receptor glycosylation. Three consensus N-linked glycosylation sites are present, two in the N-terminus and one in the putative first extracellular loop. The first ATG is believed to represent the translation initiation site because it closely approximates a Kozak consensus sequence (Kozak, 1987, Nuc. Acids Res. 15: 8125–8148) and a second cDNA clone with additional 5' sequence contains two nonsense codons in this reading frame at positions −54 and −57. Thus translation initiating at any upstream start sites would terminate before reaching the correct open reading frame. There is no polyadenylation signal and the apparent poly(A) tail most likely represents oligo(dT) priming in the 3'-untranslated region during library construction. The functional GnRH-R cDNA isolated is 1.3 kb whereas the mRNA containing this sequence is approximately 4.6 kb as determined by sucrose gradient (Sealfon et al., 1990, Mol. Endocrinol 4: 119–124) and northern blot analysis (FIG. 5B). PCR analysis of 40 positive plaques identified by primary library screening suggests that the GnRH-R mRNA contains both additional 5'-and additional 3'-untranslated sequence.

Hydrophobicity analysis of the deduced protein demonstrates seven stretches of highly hydrophobic amino acids with 20–30% sequence similarity to other GPRs with the highest degree of homology to the interleukin-8 receptor (FIG. 4). While several highly conserved residues are noted in the GnRH-R, such as the cysteines present in each of the first two extracellular loops which stabilize many receptors, several features of the GnRH-R are unusual. For example, the highly conserved transmembrane II aspartate/glutamate, which has been found to be essential for the function of many GPRs, is replaced by an asparagine. The GnRH-R is nearly the smallest member of the GPR superfamily and, unlike any other GPR, it lacks a polar cytoplasmic C-terminus. The putative first cytoplasmic loop is longer than any other GPR. Unique among GPRs, the GnRH-R may activate via dimerization (Conn et al., 1982 Nature 296: 653–655; Gregory & Taylor, 1982, Nature 300: 269–271). Its unusual structure may subserve this proposed mechanism of activation.

Another deviation from other GPRs is the substitution of serine for the conserved tyrosine located adjacent to transmembrane III. This creates a potential phosphorylation site, unique to the GnRH-R, in a domain critical for signal transduction of other GPRs. Phosphorylation of the C-terminus, which is absent in the GnRH-R, contributes to desensitization of several GPRs (see Probst et al., 1992, DNA and Cell Biology 11: 1–20). It will be interesting to determine whether the novel phosphorylation site of the GnRH-R mediates receptor desensitization. Other potential regulatory phosphorylation sites are also present (FIG. 3).

The presence of GnRH-R mRNA in a variety of neuroendocrine cell lines was studied by solution hybridization/nuclease protection assay (FIG. 5A). GnRH-R mRNA was detected in αT3-1 cells and in mouse pituitary, but not in GnRH neuron-derived (GT-1), corticotroph (AtT20) or somatolactotroph (GH3) cell lines at the limits of detection of the assay. The absence of detectable GnRH-R mRNA in the GT-1 and AtT-20 cell lines has been confirmed using higher concentrations of RNA in the solution-hybridization/nuclease protection assay (Dr. Andrea C. Gore, unpublished data). FIG. 5C shows the distribution of the GnRH-R mRNA in rat anterior pituitary. Labelling was heterogeneously distributed throughout the gland, a pattern previously observed by GnRH-R autoradiography (Badr & Pelletier, 1988, Neuropeptides 11: 7–11). Bright-field and dark-field microscopy reveals clustering of the cells expressing the GnRH-R MRNA (FIG. 5 E,F).

7. EXAMPLE

CLONING AND CHARACTERIZATION OF HUMAN GnRH-R

The subsections below describe the cloning of complementary DNA representing the human GnRH-R and confirms its identity using *Xenopus oocyte* expression. In addition, the human GnRH-R was expressed in COS-1 cells and was shown to be functionally active.

7.1. MATERIALS AND METHODS 7.1.1. CLONING OF HUMAN GnRH-R 1.2 million plaques of a GT10 human pituitary cDNA library (Clontech) were probed at high stringency (Sambrook et al., 1989 Molecular Cloning: A Laboratory Manual, Cold Spring Harbor Laboratory Press, Cold Spring Harbor, N.Y.) with the mouse GnRH-R insert (Tsutsumi et al., 1992 Mol. Endocrinol. 6:1163–1169) which had been $^{32}$P-labeled via random hexamer priming. Thirty-two positive plaques were identified on duplicate filters; ten were selected for further characterization and six successfully purified through subsequent screening. The clone with the largest insert was subcloned into the EcoRI site of pBluescript II SK$^+$ (construct LC27-4) and both strands repeatedly sequenced on an Applied Biosystems automated sequencer (Foster City, Calif., U.S.A.) using synthetic oligonucleotide primers. The sequence was analyzed using the Wisconsin GCG package on a VAX computer.

7.1.2. EXPRESSION IN *XENOPUS OOCYTES*

Construct LC27-4 was linearized and capped RNA transcript synthesized using T3 RNA polymerase. Oocyte preparation and electrophysiology were performed as previously described (Sealfon et al., 1990, Mol. Endocrinol. 4:119–124). Cells were injected with 1–10 ng of synthetic transcript and electrophysiology recorded via two-electrode voltage clamp 48 hours later. All agonists and antagonists were applied at a concentration of 0.2 µM. Antagonists were introduced into the bath 3 minutes prior to GnRH exposure.

The following GnRH analogs were used:.
GnRH-A: [D-Ala$^6$,N-Me-Leu$^7$,Pro$^9$-NHEt]GnRH; antagonist 5: [D-pGlu$^1$,D-Phe$^2$,D-Trp$^{3,6}$]GnRH; antagonist 6: [Ac-D-NaI (2) $^1$,D-α-Me-pCl-Phe$^2$,D-Trp$^3$,D-Arg$^6$,D-Ala$^{10}$]GnRH; antagonist 13: [Ac-D-NaI$^1$,D-α-4-ClPhe$^2$,D-Pal$^3$,D-Arg$^6$, D-Ala$^{10}$]GnRH; antagonist 27: [Ac-D-NaI(2)$^1$,D-α-Me-pCl-Phe$^2$,D-Trp$^3$,N-ε-ipr-Lys$^5$,D-Tyr$^6$ ,D-Ala$^{10}$] GnRH (Van der Spuy et al., 1987, in LHRH and its Analogs: Contraceptive and Therapeutic Applications (Vickery, B. H. and Nestor, J. J. eds) NTP Press, Lancaster. Buserelin [D -Ser(But)$^6$,Pro$^9$]GnRH was a generous gift of Hoerchst-Roussel Pharmaceuticals (Somerville, N.J. U.S.A.).

7.1.3. TRANSFECTION OF COS-1 CELLS

The human GnRH-R cDNA was subcloned into an expression vector, pSV2A, containing an SV40 early promoter. COS-1 cells were transiently transfected with the pSV2A-human Gn-RHR construct using the DEAE-dextran method (Keown et al., 1990, in Methods in Enzymology, VI. 185 (Goeddel, D. V., ed.) pp. 527–537, Academic Press, New York). In studies on GnRH binding, 3×10$^6$ cells/10 cm dish were transfected with 15 µg DNA. For studies on inositol phosphate production, 1.8×10$^5$ cells/well (12-well plates) were transfected with 1.5 µg DNA. Cells were assayed 48 hours after transfection.

7.1.4. RECEPTOR BINDING

Cell membranes were prepared from transfected cells with a single centrifugation step as described for rat pituitaries (Millar et al., 1989, J. Biol. Chem. 264:21007–21013). The receptor binding assay was performed as previously described (Tsutsumi et al., 1992, Mol. Endocrinol. 6:1163–1169) using $^{125}$I-GnRH-A. 10$^{-7}$M GnRH-A was used to estimated non-specific binding.

7.1.5. STIMULATION OF INOSITOL PHOSPHATE PRODUCTION

GnRH-stimulated inositol phosphate (IP) production was determined as described (Davidson et al., 1990, Endocrinology 126:80–87). Accumulation of [$^3$H]IP in the presence of LiCl was used as an index of inositol phosphate turnover. Briefly, transfected cells were labelled overnight with [$^3$H] inositol and stimulated with 1.0 µM GnRH in the presence of LiCl. The reaction was terminated by the addition of a perchloric acid solution and phytic acid. After neutralizing with KOH, the inositol phosphates were separated on a Dowex ion exchange column and counted.

7.1.6. NORTHERN BLOT AND PCR ANALYSIS

RNA was prepared from six human pituitaries (five male, one female, age 30–45) and human testis (age 80) by extraction with guanidinium thiocyanate followed by centrifugation in cesium chloride (Sambrook et al., 1989 in Molecular Cloning: A Laboratory Manual, Cold Spring Harbor Laboratory Press, Cold Spring Harbor, N.Y.). Pituitary (1.6 µg) and testis (0.9 µg) poly(A) RNA prepared using the Promega PolyA Tract mRNA isolation system was electrophoresed through a 1% agarose, 2.2M formaldehyde gel, transferred to nitrocellulose membrane (HYbond-C extra, Amersham) in 20×SSC, and fixed under vacuum at 80° C. The insert from construct LC27-4 was labelled to a specific activity of 7.2×10$^8$ cpm/µg using Amersham Megaprime Labelling Kit. Blots were prehybridized (2 h) and hybridized (overnight) in 2×Pipes, 50% formamide, 0.5% SDS, 100 µg/ml herring sperm DNA at 42° C., followed by washing (final wash 0.2×SSC, 0.1% SDS 60° C. for 10 minutes). In order to delineate the extent of 5'- and 3'-untranslated sequence in the human RNA, the clones identified on duplicate filters in the primary library screening which were not purified were used as PCR templates with pairs of primers directed against the GT10 cloning site and the known human GnRHR insert. The PCR reaction products obtained were compared with those obtained using clone LC27-4 as the PCR template on 1% agarose gels.

7.2 RESULTS

7.2.1 CLONING AND CHARACTERIZATION OF HUMAN GNRH—R

Sequencing of clone LC27-4 identified a 2160 bp insert (FIG. 9). The largest open reading frame (1008 bp) extends to the 5'-end of the clone. The translation initiation site is assigned to the first ATG in part because of the presence of a Kozak consensus sequence (Kozak, 1987 Nucleic Acids Res. 15:8125–8148). Because the clone characterized remains in reading frame in its entire 5'-extent, the existence of additional upstream initiation sites cannot be excluded. However, the presence of additional 5'- coding region is considered unlikely because of the high homology with the mouse receptor of which the translation initiation site can be assigned with greater certainly (Tsutsumi et al., 1992). The human receptor cDNA thus contains a 984 bp reading frame which encodes a 328 amino acid protein with 90% identity to the predicted sequence of the mouse receptor. The long 3'-untranslated region contains no polyadenylation signal.

Northern blot analysis was performed to determine the size of the full length human GnRHR RNA. The probe revealed a single band of ~4.7 kb in human pituitary poly(A) RNA (FIG. 10). No signal was detected in poly(A) RNA purified from human testis or with a human β-actin cDNA control. To determine the extent of the 5'- and 3'- untranslated domains of the RNA, PCR analysis of the phage isolates from the primary library screening was undertaken. An antisense oligonucleotide primer representing sequence near the 5'-end of the LC27-4 insert or a sense primer near the 3'-end of the same sequence was used in conjunction with primers designed against the adjacent GT1-cloning site to map the unpurified clones. The longest PCR products identified had ~1.3 of additional 5'-sequence and 0.3 kb of additional 3'-sequence (not shown). These data suggest that the GnRHR mRNA contains at least 1.3 kb of 5'-untranslated sequence and 1.5 kb of 3'-untranslated sequence. Based on the Northern blot data, this suggests that additional untranslated sequence (<1 kb) is not contained in any of the clones isolated.

Hydrophobicity analysis (Kyte-Dolittle) identified the seven hydrophobic domains characteristic of G=-protein coupled receptors (see FIG. 9). As was found of the predicted structure of the mouse receptor, the human GnRHR lacks essentially any C-terminal intracellular domain. Two potential N-linked glycosylation sites are present, one in each of the first two extracellular domains. Several cytoplasmic serine and threonine residues are found on intracellular domains and may serve as regulatory phosphorylation sites.

7.2.2 XENOPUS OOCYTE INJECTIONS

The largest clone isolated, LC27-4, contained a ~2.2 kb insert. To test whether this clone encoded a functional human GnRHR, synthetic RNA transcript was injected into Xenopus oocytes. All RNA-injected oocytes developed large depolarizing currents upon exposure to $2\times10^{-7}$M GnRH(n=17) or $2\times10^{-7}$M buserelin (n=6; FIG. 1) which were indistinguishable from the responses obtained following expression of the mammalian GnRHR in oocytes using tissue or cell line RNA (Sealfon et al., 1990 Mol Endocrinol. 4:119–124). These responses were completely blocked by equimolar concentrations of two potent GnRH receptor antagonists (n=5 for each; FIG. 6).

7.2.3 EXPRESSION OF HUMAN GNRH—R IN COS-1 CELLS

To further characterize the cloned human GnRHR, the receptor was expressed in COS-1 cells. Binding data using membranes from COS-1 cells transfected with the human GnRHR construct are presented in FIG. 7. The displacement of GnRH-A by GnRH-A, GnRH and antagonist 5 had dissociation constants of 0.97 nM, 2.8 nM and 8.4 nM respectively, values similar to those previously obtained with human pituitary membranes (Wormald et al., 1985 J. Clin. Endocrinol. Metab. 61:1190–1198).

The receptor expressed in COS-1 cells was functional and found to be coupled to inositophosphate metabolism. An ~8-fold increase in phosphoinositol metabolism was achieved at maximal receptor stimulation and the $EC_{50}$ of GnRH was ~3 nM. The stimulation of PI turnover induced by $(10^{-8})$ M GnRH was inhibited by a GnRH antagonist in a concentration-dependent manner (FIG. 8). GnRH-stimulated $(10^{-8}M)$ inositol phosphate production was inhibited by antagonist 13 with an $IC_{50}$ of $6.7\times10^{-9}$M and by antagonist 5 with an $IC_{50}$ of $1.05\times10^{-7}$M (not shown), giving $\kappa_d$ values of $2.1\times10^{-10}$M and $3.6\times10^{-9}$M respectively (Leslie, F. M., 1987 Pharmacol. Rev. 39:197–247).

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

---

What is claimed is:

1. An isolated nucleic acid molecule comprising a nucleotide sequence that encodes (a) a polypeptide having the amino acid sequence SEQ ID No: 2; or (b) the complement of the nucleotide sequence of (a).

2. An isolated nucleic acid molecule comprising a nucleotide sequence that hybridizes to the nucleic acid molecule of claim 1, and encodes a naturally occurring GnRH-R.

3. An isolated nucleic acid molecule comprising the nucleotide sequence of SEQ ID No: 1.

4. An isolated nucleic acid molecule comprising a nucleotide sequence that encodes (a) a polypeptide having the amino acid sequence SEQ ID No: 4; or (b) the complement of the nucleotide sequence of (a).

5. An isolated nucleic acid molecule comprising a nucleotide sequence that hybridizes to the nucleic acid molecule of claim 4, and encodes a naturally occurring GnRH-R.

6. An isolated nucleic acid molecule comprising the nucleotide sequence of SEQ ID No: 3.

7. A recombinant vector containing the nucleotide sequence of claim 1, 2, 3, 4, 5 or 6.

8. An expression vector containing the nucleotide sequence of claim 1, 2, 3, 4, 5 or 6 operatively associated with a regulatory nucleotide sequence containing transcriptional and translational regulatory information that controls expression of the nucleotide sequence in a host cell.

9. A genetically engineered cell containing the nucleic acid sequence of claim 1, 2, 3, 4, 5 or 6.

10. A genetically engineered cell containing the nucleotide sequence of claim 1, 2, 3, 4, 5 or 6 operatively associated with a regulatory nucleotide sequence containing transcriptional and translational regulatory information that controls expression of the nucleotide sequence in the host cell.

11. An isolated GnRH-R comprising the amino acid sequence of SEQ ID NO:2.

12. An isolated, naturally occurring GnRH-R encoded by a nucleotide sequence that hybridizes to the nucleic acid of SEQ ID NO:1.

13. An isolated GnRH-R comprising the amino acid sequence of SEQ ID NO:4.

14. An isolated, naturally occurring GnRH-R, encoded by a nucleotide sequence that hybridizes under highly stringent conditions to the nucleic acid of SEQ ID NO: 3.

* * * * *